US008110569B2

(12) United States Patent
Putman et al.

(10) Patent No.: US 8,110,569 B2
(45) Date of Patent: Feb. 7, 2012

(54) ENANTIOMERICALLY PURE S-ETIFOXINE, PHARMACEUTICAL COMPOSITIONS THEREOF AND METHODS OF THEIR USE

(75) Inventors: David Putman, Irvine, CA (US); Derk Hogenkamp, Carlsbad, CA (US); Olivier Dasse, Foothill Ranch, CA (US); Edward R. Whittemore, Costa Mesa, CA (US); Mark S. Jensen, Wake Forest, NC (US)

(73) Assignee: The Regents of the University of California, Oakland, CA (US)

( * ) Notice: Subject to any disclaimer, the term of this patent is extended or adjusted under 35 U.S.C. 154(b) by 195 days.

(21) Appl. No.: 11/726,289

(22) Filed: Mar. 20, 2007

(65) Prior Publication Data

US 2008/0038331 A1 Feb. 14, 2008

Related U.S. Application Data

(60) Provisional application No. 60/784,513, filed on Mar. 20, 2006.

(51) Int. Cl.
*C07D 265/18* (2006.01)
*A61K 31/536* (2006.01)

(52) U.S. Cl. ........................ 514/230.5; 544/90
(58) Field of Classification Search .............. 544/90; 514/230.5
See application file for complete search history.

(56) References Cited

U.S. PATENT DOCUMENTS

| 3,725,404 A * | 4/1973 | Kuch et al. ............... 544/90 |
| 6,638,528 B1 | 10/2003 | Kanios |
| 2007/0021415 A1 | 1/2007 | Le Guern et al. |
| 2007/0167446 A1 | 7/2007 | Verleye et al. |

FOREIGN PATENT DOCUMENTS

| DE | 3439055 A1 | 4/1986 |
| EP | 1 273 301 A2 | 1/2003 |
| EP | 1745786 | 1/2007 |

OTHER PUBLICATIONS

Hamon et al. Neuropharmacology 45 (2003), 293-303.*
Corsico et al. Psychopharmacologia (Berl.) 45, 301-303 (1976).*
Vippagunta et al, "Crystalline Solids" Advanced Drug Delivery Reviews, vol. 48, pp. 3-26 (2001).*
Aladro, et al., Enantioselective Synthesis of α-Hydroyacids Through Oxidation of Terminal Alkenes with AD-mix/TEMPO, Tetrahedron Letters 41(17):3209-13 (00/00/2000).
Baldwin, et al., The Synthesis of 4-arylsufanyl-substituted Kainoid Analogues from trans-4-hydroxy-$_L$-proline,Tetrahedron 57(37):7991-97 (00/00/2001).
Blanco, et al., Chiral Sulfinic Acids: Synthesis of Sodium (*IS, 2S, 5R*)-2-Isopropyl-5-methylcyclohexanesufinate by a Novel Route, Tetrahedron 51(3):935-40 (00/00/1995).

Blanco, et al., Synthesis of Chiral Sulfinic Acids: Sodium(1*S-exo*)-2-Bornanesulfinate, Synthesis 7:584-86 (00/00/1989).
Corisco, et al., Evaluation of the Psychotropic Effect of Etifoxine Through Pursuit Rotor Performance and GSR, Psychopharmacologia (Berl.) 45:301-03 (00/00/1976).
Csomos, et al., Synthesis and Transformations of 2-(phenylhydroxymethyl)cyclohexylamines, Tetrahedron, 57(15):3175-83 (00/00/2001).
Dale, et al., Nuclear Magnetic Resonance Enantiomer Reagents. Configurational Correlations *via* Nuclear Magnetic Resonance Chemical Shifts of Diastereomeric Mandelate, *O*-Methylmandelate, and α-Methoxy-α-trifluoromethylphenylacetate, MTPA) Esters, J. Am. Chem. Soc. 95(2):512-19 (Jan. 24, 1973).
Dosa, et al., Catalytic Asymmetric Addition of $ZnPh_2$ to Ketones: Enantioselective Formation of Quaternary Stereocenters, J. Am. Chem. Soc. 120(2):445-46 (Jan. 1, 1998).
Forrat, et al., Chiral Tertiary Alcohols from a *trans*-1-arenesulfonyl-amino-2-isobomeolsulfonylaminocyclohexane-catalyzed Addition of Organizincs to Ketones, Tetrahedron: Asymmetry 16:3341-44 (00/00/2005).
Garcia, et al., Highly Enantioselective Catalytic Phenylation of Ketones with a Constrained Geometry Titanium Catalyst, Org. Letters 5(20) 3641-44 (00/00/2003), Including Supporting Information, pp. S1-S31.
Hamon, et al., The Modulatory Effects of the Anxiolytic Etifoxine of $GABA_A$ Receptors are Mediated by the β Subunit, Neuropharmacology, 45:293-03 (00/00/2003).
Hoeve, et al., The Design of Resolving Agents. Chiral Cyclic Phosphoric Acides, J. Org. Chem. 50(23):4508-14 (00/00/1985).
Hole, et al., The Tail-Flick and Formalin Tests in Rodents: Changes in Skin Temperature as a Confounding Factor, Pain 53:247-54 (00/00/1993).
Hubner, et al., Uber die Umsetzung von Hydroxysteroiden mit Carbodiimiden, J. fur Praktische Chemie. (Leibzig) 311(4) 630-34 (00/00/1969).
Matsugi, et al., A Novel Separation Technique of Diastereomeric Esters of Pyridylethanols by Extraction: Formal Total Synthesis of PNU-142721, HIV-1 Reverse Transcriptase Inhibitor, Tetrahedron 60(14):3311-17 (00/00/2004).
Pierce, et al., Practical Asymmetric Synthesis of Efavirenz (DMP 266), and HIV-1 Reverse Transcriptase Inhibitor, J. Org. Chem. 63(23):8536-43 (00/00/1998).
Prieto, et al., Highly Enantioselective Arylation of Ketones, Tetrahedron: Asymmetry, 14:1955-57 (00/00/2003).
Ravi, et al., Thermal Fries Rearrangement of Anilides, Indian J. Chem. 30B(4):443-45 (04/00/1991).
Saito, et al., Synthesis of Alkyl-β-$_D$-thioglucopyranosides, a Series of New Nonionic Detergents, Chem. Pharm. Bull. 33(2):503-08 (00/00/1985).

(Continued)

*Primary Examiner* — Kahsay T Habte
(74) *Attorney, Agent, or Firm* — Cooley LLP

(57) ABSTRACT

Enantiomerically pure S-etifoxine and pharmaceutically acceptable salts, solvates, hydrates or prodrugs thereof are provided. Also provided are pharmaceutical compositions comprising the compounds and methods of treating disorders associated with central nervous system using the compounds and pharmaceutical compositions.

47 Claims, 10 Drawing Sheets

OTHER PUBLICATIONS

Sanki, et al., Synthesis of Anomerically Pure Vinyl Sulfone-Modified Pent-2-Enofuranosides and Hex-2-Enopyranosides: A Group of Highly Reactive Michael Acceptors for Acessing Carbohydrate Based Synthons, Tetrahedron 59(36):7203-14 (00/00/2003).

Schaus, et al., Highly Selective Hydrolytic Kinetic Resolution of Terminal Epoxides Catalyzed by Chiral (salen)Co$^{III}$ Complexes. Practical Synthesis of Enantioenriched Terminal Epoxides and 1,2-Diols, J. Am. Chem. Soc. 124(7):1307-15 (00/00/2000), Including Supporting Information, pp. S1-S23.

Su, et al., Fries-Type Rearrangement of Acylanilides in the Ytterbium Triflate, J. Chem. Res. 9:611-13 (00/00/2004).

Uozumi, Cationic Palladium/Boxax Complexes for Catalytic Asymmetric Wacker-Type Cyclization, J. Org. Chem. 63(15):5071-75 (00/00/1998), Including Supporting Information, pp. i-ix.

Uozumi, et al., Design and Preparation of 3.3'-Disubstituted 2.2'-Bis(oxazoly1)-1.1'-Binaphthyls (Boxax): New Chiral Bis(oxazoline) Ligands for Catalytic Asymmetric Wacker-Type Cyclization, J. Org. Chem. 64(5):1620-25 (00/00/001999), Including Supporting Information, pp. 1-10.

Whittemore, et al., Pharmacology of the Human γ-Aminobutyric Acid$_A$ Receptor α4 Subunit Expressed in *Xenopus laevis* Oocytes, Mole. Pharm. 50:1364-75 (00/00/1996).

Yoder, The Replacement of Secondary Hydroxyl Groups by Sulfonic Acid Substitutents, Iowa State College, Chem Sec. of Iowa Agr. Exp. Station, 20(Paper No. J 2751):1317-21, (10/00/1955).

Tsang et al., *Curr Pharm Des*. 2004; 10(9):1035-44.

Dawson et al., *CNS Spectr*. 2005 ;10(1): 21-7.

Lydiard R.D. *J Clin Psychiatry*. 2003, 64 Suppl 3:21-7.

Anthony Krantis, *News Physiol. Sci*. 15, 2000.

European Patent Application 07753576 Office Action mailed Nov. 29, 2010.

European Patent Application 07753576 Office Action mailed Feb. 11, 2011.

\* cited by examiner

ENANTIOMERICALLY PURE S-ETIFOXINE, PHARMACEUTICAL COMPOSITIONS THEREOF AND METHODS OF THEIR USE

This application claims priority to U.S. provisional application Ser. No. 60/784,513, filed Mar. 20, 2006, entitled "Enantiomerically Pure (−)-Etifoxine, Pharmaceutical Compositions Thereof And Methods Of Their Use". The disclosure of the above referenced application is incorporated by reference herein in its entirety.

FIELD OF THE INVENTION

Provided herein are S-etifoxine and pharmaceutically acceptable salts, solvates, hydrates and prodrugs thereof, compositions comprising the same and methods of using the compounds and compositions.

BACKGROUND OF THE INVENTION

Etifoxine is chemically named as [6-chloro-2-(ethylamino)-4-methyl-4-phenyl-4H-3,1-benzoxazine]. A hydrochloride salt of etifoxine, Stresam, is sold in France for the treatment of anxiety. Etifoxine was originally disclosed in U.S. Pat. No. 3,725,404. Although etifoxine is chiral, as far as the inventors are aware, there is no disclosure of its resolution or asymmetric synthesis. Etifoxine has a depressive effect on the central nervous system and is an anticonvulsant. It is also known to have tranquilizing effects, narcosis-prolonging effects and analgesic properties. See, e.g., Corisco et al., *Psychopharmacologia (Berl.)* 45, 301-303, 1976.

Etifoxine hydrochloride has been extensively studied and reportedly can be used in the treatment of a variety of disorders. For example, European Patent No. EP1273301, German Patent No. DE3439055 and U.S. Pat. Nos. 3,725,404 and 6,638,528 disclose uses of etifoxine as an anticonvulsant, a tranquilizer and an anxiolytic drug. It has been reported to act as a modulator of GABA receptor complex activity. See, Hamon et al., 2003, *Neuropharmacology,* 45, 293-303.

There remains a need for methods of using the same for treating anxiety and other conditions.

SUMMARY OF THE INVENTION

Provided herein are pure (−)-etifoxine and salts, solvates, hydrates and prodrugs thereof. Also provided are compositions comprising pure (−)-etifoxine or a salt, solvate, hydrate or prodrug thereof and a pharmaceutical carrier, excipient or diluent.

The compounds and compositions are useful, for example, in methods for treating, preventing, ameliorating or managing symptoms of diseases or disorders amenable to treatment, prevention, amelioration or management with racemic etifoxine. In certain embodiments, provided herein are methods for treating, preventing, ameliorating or managing symptoms of diseases or disorders including, but not limited to conditions associated with anxiety, convulsions, disorders of the central nervous system and mental disorders. Disorders of the central nervous system include but are not limited to multiple sclerosis, muscle relaxation in spinal spasticity, cerebral palsy, trigeminal neuralgia, migraine, Alzheimer's disease, pain, drug withdrawal symptoms and convulsive disorders, such as epilepsy. Mental disorders include, but are not limited to, anxiety disorders; mood disorders; sleep disorders; delirium, dementia and amnestic and other cognitive disorders; attention deficit and disruptive behavior disorders; and substance related disorders. In certain embodiments, the compounds and compositions are useful in methods for treating, preventing, ameliorating or managing symptoms of diseases or disorders associated with cardiovascular disorders such as hypertension, and gut motility disorders such as irritable bowel syndrome. The methods provided herein comprise administering to a subject in need thereof an effective amount of enantiomerically pure (−)-etifoxine, or a salt, solvate, hydrate or prodrug thereof substantially free of the other enantiomer.

In particular embodiments, enantiomerically pure (−)-etifoxine is useful for the treatment or prevention of anxiety with little or no sedating side effects. In further particular embodiments, enantiomerically pure (−)-etifoxine is useful for the treatment or prevention of pain, e.g. neuropathic pain, with little or no sedating side effects.

The absolute configuration of (+)-etifoxine was determined to be R by X-ray crystallographic analysis as described in the examples below. (−)-Etifoxine was assigned to be the corresponding S enantiomer.

DETAILED DESCRIPTION OF THE INVENTION

Definitions

Figure 1:
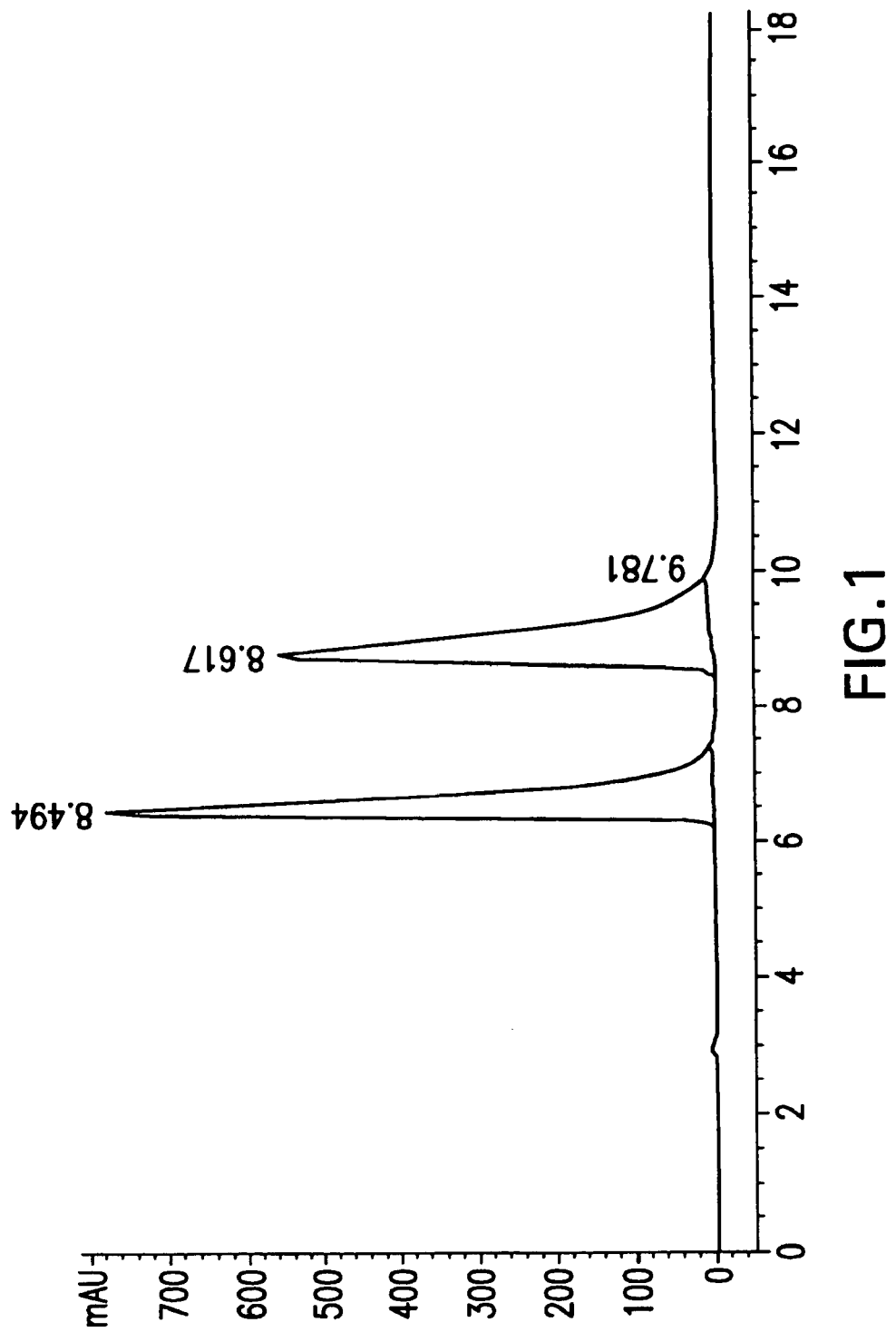
FIG. 1 provides an HPLC trace illustrating resolution of the two enantiomers of etifoxine by chiral HPLC—the two peaks in the trace, peak 1 and peak 2, correspond to pure enantiomers of etifoxine.

Unless defined otherwise, all technical and scientific terms used herein have the same meaning as is commonly understood by one of ordinary skill in the art. All patents, applications, published applications and other publications are incorporated by reference in their entirety. In the event that there are a plurality of definitions for a term herein, those in this section prevail unless stated otherwise.

As used herein pure S-etifoxine is substantially free from R-etifoxine (i.e., in enantiomeric excess). In other words, the "S" form of etifoxine is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of the enantiomer. In certain embodiments, the weights are based upon total weight of etifoxine.

As used herein and unless otherwise indicated, the term "enantiomerically pure R-etifoxine" refers to at least about 80% by weight R-etifoxine and at most about 20% by weight S-etifoxine, at least about 90% by weight R-etifoxine and at most about 10% by weight S-etifoxine, at least about 95% by weight R-etifoxine and at most about 5% by weight S-etifoxine, at least about 99% by weight R-etifoxine and at most about 1% by weight S-etifoxine, at least about 99.9% by weight R-etifoxine or at most about 0.1% by weight S-etifoxine. In certain embodiments, the weights are based upon total weight of etifoxine.

As used herein and unless otherwise indicated, the term "enantiomerically pure S-etifoxine" or "S-etifoxine" refers to at least about 80% by weight S-etifoxine and at most about 20% by weight R-etifoxine, at least about 90% by weight S-etifoxine and at most about 10% by weight R-etifoxine, at least about 95% by weight S-etifoxine and at most about 5% by weight R-etifoxine, at least about 99% by weight S-etifoxine and at most about 1% by weight R-etifoxine or at least about 99.9% by weight S-etifoxine and at most about 0.1% by weight R-etifoxine. In certain embodiments, the weights are based upon total weight of etifoxine.

In the compositions provided herein, enantiomerically pure S-etifoxine or a pharmaceutically acceptable salt, solvate, hydrate or prodrug thereof can be present with other active or inactive ingredients. For example, a pharmaceutical composition comprising enantiomerically pure S-etifoxine can comprise, for example, about 90% excipient and about 10% enantiomerically pure S-etifoxine. In certain embodiments, the enantiomerically pure S-etifoxine in such compositions can, for example, comprise, at least about 99.9% by weight S-etifoxine and at most about 0.1% by weight R-etifoxine. In certain embodiments, the active ingredient can be formulated with little or no excipient or carrier.

The term "$GABA_A$ receptor" refers to a protein complex that detectably binds GABA and mediates a dose dependent alteration in chloride conductance and membrane polarization. Receptors comprising naturally-occurring mammalian (especially human or rat) $GABA_A$ receptor subunits are generally preferred, although subunits may be modified provided that any modifications do not substantially inhibit the receptor's ability to bind GABA (i.e., at least 50% of the binding affinity of the receptor for GABA is retained). The binding affinity of a candidate $GABA_A$ receptor for GABA may be evaluated using a standard ligand binding assay known in the art. There are a variety of $GABA_A$ receptor subtypes that fall within the scope of the term "$GABA_A$ receptor." These subtypes include, but are not limited to, $\alpha_{1-}$, $\beta_{1-3}$, $\gamma_{1-3}$, $\pi$, $\theta$, $\epsilon$, $\delta$, and $\rho_{3-1}$ receptor subtypes. $GABA_A$ receptors may be obtained from a variety of sources, such as from preparations of rat cortex or from cells expressing cloned human $GABA_A$ receptors. Particular subtypes may be readily prepared using standard techniques (e.g., by introducing mRNA encoding the desired subunits into a host cell, as described herein).

As used herein and unless otherwise indicated, the terms "treat," "treating" and "treatment" refer to alleviating or reducing the severity of a symptom associated with the disease or condition being treated. For example, the terms "treating anxiety" and "treatment of anxiety" refer to relief from one or more symptoms associated with anxiety diseases. Diseases or disorders associated with anxiety can be categorized in the following: panic disorder without agoraphobia, panic disorder with agoraphobia, agoraphobia without history of panic disorder, specific phobia, social phobia, obsessive compulsive disorder, posttraumatic stress disorder, acute stress disorder, generalized anxiety disorder, anxiety disorder due to a medical condition, substance induced anxiety disorder, anxiety disorder not otherwise specified (NOS). Symptoms associated with anxiety diseases include, but are not limited to, skin blanching, faintness, dilated pupils, elevated blood pressure, dizziness, sweating, sense of fecal or urinary urgency, headache, sinking feeling, chest pain, nausea, palpitations, abdominal distress, dysphoria, muscular tension, distractibility, insomnia, irritability, fatigue, choking and restlessness.

As used herein, a "CNS disorder" is a disease or condition of the central nervous system that can be treated, prevented, managed or ameliorated with a compound or composition provided herein. Certain CNS disorders are responsive to $GABA_A$ receptor modulation in a subject. Exemplary CNS disorders include multiple sclerosis, muscle relaxation in spinal spasticity, cerebral palsy, trigeminal neuralgia, migraine, Alzheimer's disease, pain, drug withdrawal symptoms and convulsive disorders such as epilepsy. Particular pain disorders include neuropathic pains such as diabetic neuropathy, peripheral neuropathy and post-herpetic neuralgia.

As used herein, a "mental disorder" is a disorder of the American Psychiatric Association's Diagnostic and Statistical Manual of Mental Disorders, $4^{th}$ edition (DSM-IV) that can be treated, prevented, managed or ameliorated with a compound or composition provided herein. Exemplary mental disorders include anxiety disorders (panic disorder without agoraphobia, panic disorder with agoraphobia, agoraphobia without history of panic disorder, specific phobia, social phobia, obsessive compulsive disorder, posttraumatic stress disorder, acute stress disorder, generalized anxiety disorder, anxiety disorder due to a medical condition, substance induced anxiety disorder, anxiety disorder not otherwise specified (NOS)), mood disorders (depressive disorder, e.g. major depressive disorder—single episode or recurrent, dysthymic disorder, depressive disorder NOS; bipolar disorder, e.g. bipolar I disorder, bipolar II disorder, cyclothymic disorder, bipolar disorder NOS, mood disorder due to general medical condition, substance-induced mood disorder, mood disorder NOS), sleep disorders (primary sleep disorder, e.g. primary insomnia, primary hypersomnia, narcolepsy, breathing-related sleep disorder, circadian rhythm sleep disorder, dyssomnia NOS; parasomnia, e.g. nightmare disorder, sleep terror disorder, sleepwalking disorder, parasomnia NOS; sleep disorder secondary to another mental disorder, e.g. sleep disorder secondary to anxiety disorder, mood disorder and/or other mental disorder; sleep disorder due to general medical condition and substance-induced sleep disorder), delirium, dementia and amnestic and other cognitive disorders (delirium; dementia, e.g. dementia of Alzheimer's type, vascular dementia, dementia due to HIV disease, dementia due to head trauma, dementia due to Parkinson's disease, dementia due to Huntington's disease, dementia due to Pick's disease, dementia due to Creutzfeldt-Jakob disease, dementia due to general medical condition, substance-induced dementia, dementia due to multiple etiologies, dementia NOS; amnestic disorders, e.g. amnestic disorder due to general medical condition, substance-induced amnestic disorder, amnestic disorder NOS; cognitive disorder NOS) attention deficit and disruptive behavior disorders (attention deficit/hyperactivity disorder—combined type, predominantly inattentive type and predominantly hyperactive-impulsive type; attention deficit/hyperactivity disorder NOS; conduct disorder, oppositional defiant disorder and disruptive behavior disorder NOS) and substance related disorders. Further mental disorders and criteria for those disorders are described in the American Psychiatric Association's Diagnostic and Statistical Manual of Mental Disorders, 4$^{th}$ edition (DSM-IV), the contents of which are hereby incorporated by reference in their entirety.

As used herein and unless otherwise indicated, the terms "manage," "managing" and "management" refer to maintaining a reduction in severity or avoidance of a symptom associated with the disease or condition being managed.

As used herein and unless otherwise indicated, the term "pharmaceutically acceptable salt" refers to a salt prepared from a pharmaceutically acceptable non-toxic inorganic or organic acid. Inorganic acids include, but are not limited to, hydrochloric, hydrobromic, hydroiodic, nitric, sulfuric, and phosphoric. Organic acids include, but are not limited to, aliphatic, aromatic, and sulfonic organic acids including, but are not limited to, camphorsulfonic, mandelic, tartaric, citric, fumaric, gluconic, isethionic, para-toluenesulfonic, glycolic, glucuronic, furoic, glutamic, anthranilic, salicylic, embonic (pamoic), methanesulfonic, ethanesulfonic, panthothenic, benzenesulfonic, sulfanilic, alginic, ascorbic and galacturonic acid.

As used herein "subject" is an animal, typically a mammal, including human, such as a patient.

As used herein, and unless otherwise specified, the term "solvate" refers to a compound provided herein or a salt thereof, that further includes a stoichiometric or non-stoichiometric amount of solvent bound by non-covalent intermolecular forces. Where the solvent is water, the solvate is a hydrate.

As used herein, the IC$_{50}$ refers to an amount, concentration or dosage of a particular test compound that achieves a 50% inhibition of a maximal response in an assay that measures such response.

As used herein, and unless otherwise specified, the terms "therapeutically effective amount" and "effective amount" of a compound refer to an amount sufficient to provide a therapeutic benefit in the treatment, prevention and/or management of a disease, to delay or minimize one or more symptoms associated with the disease or disorder to be treated. The terms "therapeutically effective amount" and "effective amount" can encompass an amount that improves overall therapy, reduces or avoids symptoms or causes of disease or disorder, or enhances the therapeutic efficacy of another therapeutic agent.

The terms "co-administration" and "in combination with" include the administration of two therapeutic agents (for example, S-etifoxine and lorazepam) either simultaneously, concurrently or sequentially with no specific time limits. In one embodiment, both agents are present in a subject at the same time or exert their biological or therapeutic effect at the same time. In one embodiment, the two therapeutic agents are in the same composition or unit dosage form. In another embodiment, the two therapeutic agents are in separate compositions or unit dosage forms.

Compounds of the Invention

Etifoxine is a chiral molecule that has been used as a racemate. Etifoxine is 6-chloro-2-(ethylamino)-4-methyl-4-phenyl-4H-3,1-benzoxazine and can be represented by the following chemical structure:

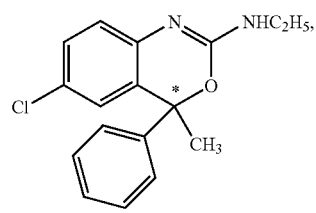

where * indicates the chiral center in the molecule.
Etifoxine hydrochloride is represented as:

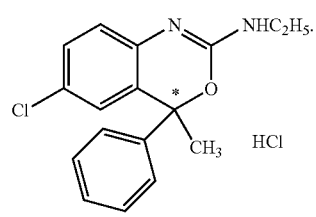

U.S. Pat. No. 3,725,404 describes various methods of preparing and using etifoxine as racemic mixture, the contents of which are hereby incorporated by reference in their entirety.

In certain embodiments, provided herein is a compound according to the formula:

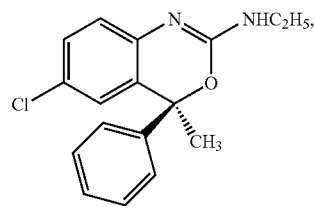

or a pharmaceutically acceptable salt, solvate, hydrate or prodrug thereof.

In certain embodiments, provided herein is a compound according to the formula:

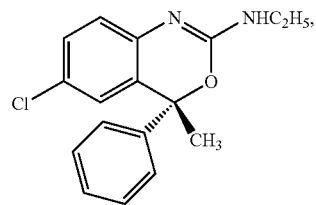

or a pharmaceutically acceptable salt, solvate, hydrate or prodrug thereof.

The absolute configuration of (+)-etifoxine was determined to be R by derivatization with a chiral adduct followed by X-ray crystallographic analysis as described in the examples below. (−)-Etifoxine was assigned to be the corresponding S enantiomer.

In certain embodiments, the compound is selected from enantiomerically pure S-etifoxine and pharmaceutically acceptable salts, solvates, hydrates and prodrugs thereof. In certain embodiments, the compound is selected from enantiomerically pure S-etifoxine and pharmaceutically acceptable salts thereof. In certain embodiments, the compound is S-etifoxine hydrochloride.

In certain embodiments, the enantiomerically pure S-etifoxine comprises at least about 80% by weight S-etifoxine and at most about 20% by weight R-etifoxine, at least about 90% by weight S-etifoxine and at most about 10% by weight R-etifoxine, at least about 95% by weight S-etifoxine and at most about 5% by weight R-etifoxine, at least about 96.6% by weight S-etifoxine and at most about 3.4% by weight R-etifoxine, at least about 97% by weight S-etifoxine and at most about 3% by weight R-etifoxine, at least about 99% by weight S-etifoxine and at most about 1% by weight R-etifoxine or at least about 99.9% by weight S-etifoxine and at most about 0.1% by weight R-etifoxine. In one embodiment, the pure S-etifoxine comprises at least about 96.6% by weight S-etifoxine and at most about 3.4% by weight R-etifoxine, at least about 97% by weight S-etifoxine and at most about 3% by weight R-etifoxine, at least about 98% by weight S-etifoxine and at most about 2% by weight R-etifoxine or at least about 99% by weight S-etifoxine and at most about 1% by weight R-etifoxine. In certain embodiments, the weights are based upon total weight of etifoxine.

In certain embodiments, the pure enantiomer has improved activity as a GABA modulator. In certain embodiments, the compounds are active as anxiolytics. In certain embodiments, the compounds are active as anticonvulsants, tranquilizers and have narcosis-prolonging effects or analgesic properties.

In the description herein, if there is any discrepancy between a chemical name and structure, the structure preferably controls.

Methods for Preparation and Isolation of Pure Enantiomers

The S-etifoxine compounds provided herein may be prepared according to any techniques known to those of skill in the art. For instance, they may be prepared by chiral or asymmetric synthesis from a suitable optically pure precursor or obtained from etifoxine racemate by any conventional technique, for example, by chromatographic resolution using a 'chiral' column, TLC or by the preparation of diastereoisomers, separation thereof and regeneration of the desired enantiomer. See, e.g., "Enantiomers, Racemates and Resolutions," by J. Jacques, A. Collet, and S. H. Wilen, (Wiley-Interscience, New York, 1981); S. H. Wilen, A. Collet, and J. Jacques, *Tetrahedron*, 2725 (1977); E. L. Eliel *Stereochemistry of Carbon Compounds* (McGraw-Hill, NY, 1962); and S. H. Wilen *Tables of Resolving Agents and Optical Resolutions* 268 (E. L. Eliel ed., Univ. of Notre Dame Press, Notre Dame, Ind., 1972, *Stereochemistry of Organic Compounds*, Ernest L. Eliel, Samuel H. Wilen and Lewis N. Manda (1994 John Wiley & Sons, Inc.), and *Stereoselective Synthesis A Practical Approach*, Mihály Nógrádi (1995 VCH Publishers, Inc., NY, N.Y.).

In certain embodiments, S-etifoxine may be obtained by reaction of the racemate with a suitable optically active acid. Suitable acids include, but are not limited to, optically pure chiral sulfonic acids, optically pure chiral phosphoric acids, including chiral cyclic phosphoric acids, and optically pure α-methoxy-alpha-(trifluoromethyl) phenylacetic acid (Mosher's acid). Exemplary useful chiral acids include camphor-sulfonic acids, such as camphor-10-sulfonic acid, 3-bromo-camphor-10-sulfonic acid, 3-bromo-camphor-8-sulfonic acid and 9,7-dibromo-camphor-10-sulfonic acid; 4-(2-chlorophenyl)-5,5-dimethyl-2-hydroxyl-1,3,2-dioxaphosphorinane 2-oxide, 5,5-dimethyl-2-hydroxy-4-(methoxyphenyl)-1,3,2-dioxaphosphorinane 2-oxide, 5,5-dimethyl-2-hydroxy-4-(dichlorophenyl)-1,3,2-dioxaphosphorinane 2-oxide and 5,5-dimethyl-2-hydroxy-4-phenyl-1,3,2-dioxaphosphorinane 2-oxide; tartaric acid, such as dibenzoyl tartaric acid and phosphoric acids such as binaphthyl phosphoric acid and mono-1-methyl phosphoric acid (Bighley et al., 1995, *Salt Forms of Drugs and Adsorption, in Encyclopedia of Pharmaceutical Technology*, vol. 13, Swarbrick & Boylan, eds., Marcel Dekker, New York; ten Hoeve & H. Wynberg, 1985, *Journal of Organic Chemistry* 50:4508-4514; Dale & Mosher, 1973, *J. Am. Chem. Soc.* 95:512; and *CRC Handbook of Optical Resolution via Diastereomeric Salt Formation*, the contents of which are hereby incorporated by reference in their entireties).

Optically pure isomers of etifoxine can be recovered either from the crystallized diastereomer or from the mother liquor, depending on the solubility properties of the particular acid resolving agent employed and the particular acid enantiomer used. The identity and optical purity of the particular etifoxine isomer so recovered can be determined by polarimetry or other analytical methods known in the art. The diasteroisomers can then be separated, for example, by chromatography or fractional crystallization, and the desired enantiomer regenerated by treatment with an appropriate base or acid. The other enantiomer may be obtained from the racemate in a similar manner or worked up from the liquors of the first separation. Each of the resulting enantiomers may be converted to a hydrochloride salt using conventional techniques, for example, by treatment with hydrochloric acid.

In certain embodiments, optically pure enantiomers of etifoxine can be separated from racemic etifoxine by chiral chromatography. Various chiral columns and eluents for use in the separation of the enantiomers are available and suitable conditions for the separation can be empirically determined by methods known to one of skill in the art. Exemplary chiral columns available for use in the separation of the enantiomers provided herein include, but are not limited to CHIRALCEL® OB, CHIRALCEL® OB-H, CHIRALCEL® OD, CHIRALCEL® OD-H, CHIRALCEL® OF, CHIRALCEL® OG, CHIRALCEL® OJ and CHIRALCEL® OK. Exemplary conditions using CHIRALCEL® OF column for the separation of the two enantiomers of etifoxine are described in Example 1.

In certain embodiments, an enantiomer of etifoxine can be prepared by asymmetric synthesis. For instance, in certain embodiments, an enantiomer of etifoxine can be prepared from tertiary alcohol 1 (Scheme A). Tertiary alcohol 1 can be prepared as a single enantiomer, for example, by reacting phenylzinc with 2-amino-4-chloroacetophenone (2) in the presence of a suitable chiral reagent as described by Garcia and Walsh, 2003, *Organic Lett.* 5(20):3641 and Dosa and Fu, 1998, *J. Am. Chem. Soc.* 120(2):445-6, the contents of which are hereby incorporated by reference in their entireties. The starting acetophenone 2 can be prepared, for example, from commercially available 4-chloroacetanilide as described by Su and Jin, 2004, *Journal of Chemical Research* 9:611-613 and Ravi et al., 1991, *Indian Journal of Chemistry, Section B: Organic Chemistry Including Medicinal Chemistry*, 30B(4): 443-5, the contents of which are hereby incorporated by reference in their entireties.

Scheme A

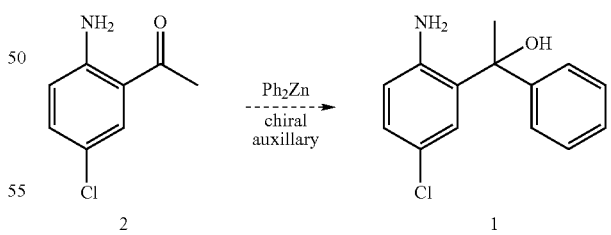

Tertiary alcohol 1 can also be prepared as a single enantiomer by conversion of the corresponding racemic alcohol to a diasteromeric salt with an appropriate chiral acid such as (1S)-(+)-camphorsulfonic acid or its antipode followed by fractional crystallization.

Alcohol 1 can also be conjugated with a chiral auxiliary and the resulting diastereomers separated using known methods (such as chromatography, fractional crystallization, etc.) as shown in Scheme B. R*LG is a single enantiomer that is used as an alkylating or acylating agent.

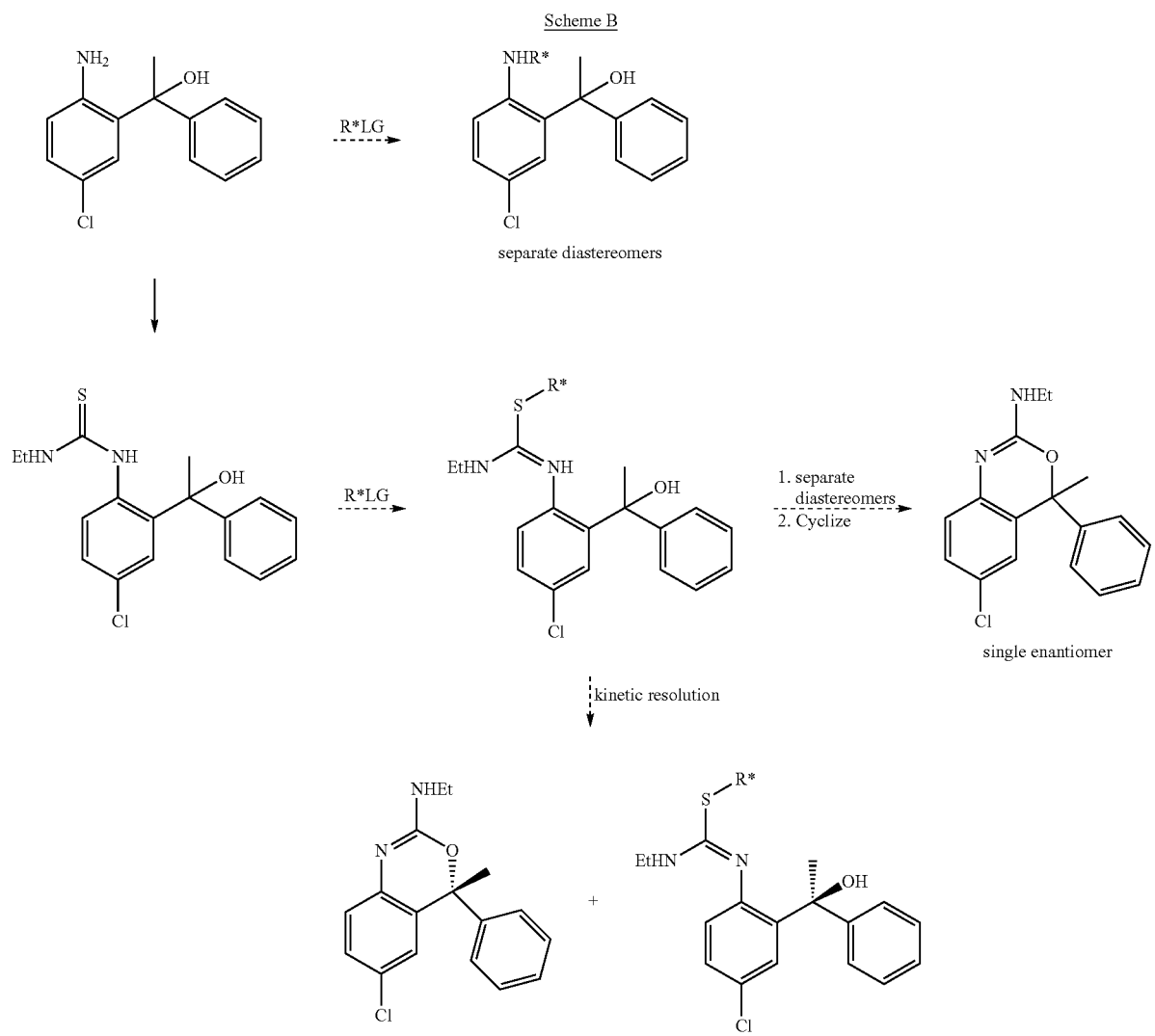

Exemplary alkylating agents include methanesulfonates derived from (−) and (+)-menthol (Blanco et al., 1995, *Tetrahedron* (1995), 51(3), 935-40.) and the tosylate prepared from (−)-borneol (Blanco, et al., 1990, *Synthesis* 7:584-6 and Yoder, 1955, *Journal of Organic Chemistry* 20:1317-21, the contents of which are hereby incorporated by reference in their entireties). In addition, 1, 2:5,6-di-O-isopropylidene-α-D-glucofuranose (3, Scheme C) can be converted to the corresponding methanesulfonate (Sanki, et al., 2003, *Tetrahedron* 59(36):7203, the contents of which are hereby incorporated by reference in their entirety). Glucose pentaacetate, acetobromo-α-D-glucose (4, Scheme C) and 2,3,4,6-tetraacetyl-α-D-galactopyranosyl bromide (5, Scheme Scheme C

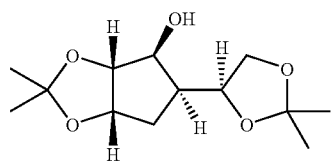
3

-continued

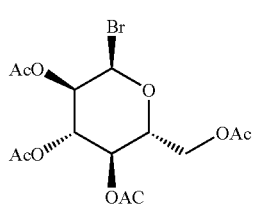
4

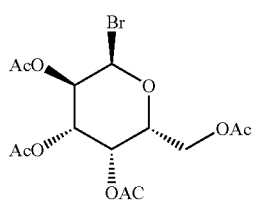
5

C) react with thioureas to form S-alkylated products using the method of Saito and Tsuchiya (*Chem. Pharm. Bull.,* 1985, 33(2):503, the contents of which are hereby incorporated by reference in their entirety). The alkylation of the thioamide with the enantiomers of 1-phenylethanol can be accomplished using the methods of *Tetrahedron,* 2004, 60(14):3311, *Tetrahedron,* 2001, 57(37):7991 and *Tetrahedron,* 2001, 57(15):3175, the contents of which are hereby incorporated by reference in their entireties. Sterols can also be employed as chiral alkylating agents when properly activated (Huebner et al., 1969, *Journal fuer Prackische Chemie (Leibzig)* 311(4):630, the contents of which are hereby incorporated by reference in their entirety). Once the thioamide is alkylated, the corresponding diastereomers can be separated by standard techniques as described above or the diastereomers can be subjected to kinetic resolution, in which one diastereomer forms a single enantiomer of etifoxine while leaving the second diastereomer uncyclized.

Tertiary alcohol 1 can also be prepared as a single enantiomer from the enantiomerically pure epoxide as shown in Scheme D. The epoxide can be prepared, for example, by direct enantiospecific epoxidation of a 1,1-diaryl substituted alkene or via the enantiospecific conversion of the alkene to a 1,2-diol and subsequent formation of the epoxide. The epoxide can also be prepared by hydrolytic kinetic resolution of the corresponding racemic epoxide using, for example, Jacobsen's catalyst (see, e.g., Schaus et al., 2000, *J. Am. Chem. Soc.* 124:1307-1315). The diol formation can be carried out using the method described in *Tetrahedron Lett.,* 2000, 41(17):3209, the contents of which are hereby incorporated by reference in their entirety.

In further embodiments, S-etifoxine can be prepared by selective cyclization of an appropriate diaryl alkene as illustrated in Scheme E, below. Useful chiral ligands are provided in, for example, *J. Org. Chem.,* 1998, 63:5071 and *J. Org. Chem.,* 1999, 64:1620, the contents of which are incorporated by reference in their entirety.

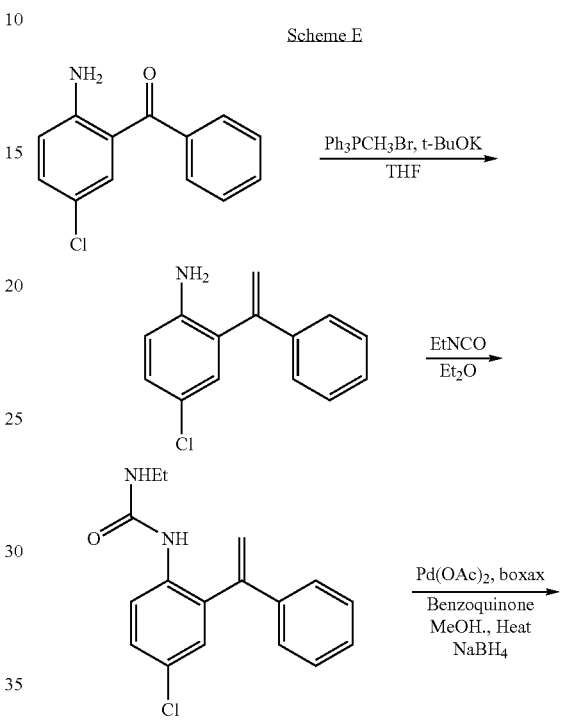

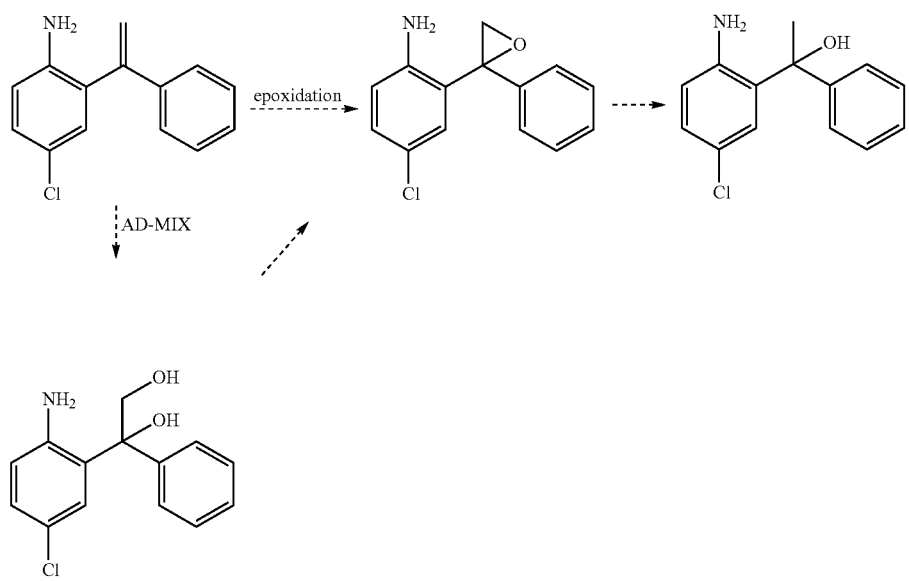

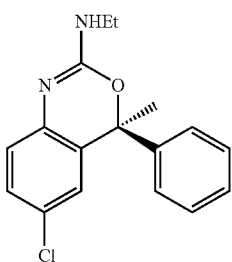

In further embodiments, S-etifoxine can be prepared by selective reaction of an appropriate phenone as illustrated in Scheme F, below. Useful chiral reagents are provided in, for example, *Tetrahedron: Asymmetry,* 14 (2003), 1955, *J. Am. Chem. Soc.* 1998, 120, 445, *Org. Letters,* 2003, 5, 3641, *Tetrahedron: Asymmetry,* 16 (2005), 3341, *J. Org. Chem.,* 1998, 63, 8536, the contents of which are incorporated by reference in their entireties.

In still further embodiments, the etifoxine enantiomer can be prepared by addition of an appropriately substituted phenyl group to acetophenone (Scheme G). This may be done by selective deprotonation of the phenyl moiety by an alkyl lithium or alternatively by using an appropriate Grignard reagent. Also, the phenyl moiety may be converted to the corresponding diphenyl zinc and added in the presence of an asymmetric catalyst (or stoichiometric) to acetophenone (see Prieto et al., 2003, *Tetrahedron Assym* 14(14), 1955, and Garcia et al., 2003, *Org. Lett.* 5(20):3641, the contents of which are hereby incorporated by reference in their entireties). The addition of the phenyl group may be conducted in the presence of a Lewis Acid, such as titanium tetraisopropoxide. The resultant molecule could then be deprotected and reacted with ethyl isothiocyanate to give a "thiourea." The "thiourea" is then alkylated using, for instance, methyl iodide, and the resultant S-Me thiourea is displaced intramolecularly under, for example, basic conditions, by the previously prepared hydroxyl group. Alternatively, the S-Me group may be oxidized using a compatible oxidant (such as m-CPBA) to $SO_2Me$ and then displaced intramolecularly by the hydroxyl group.

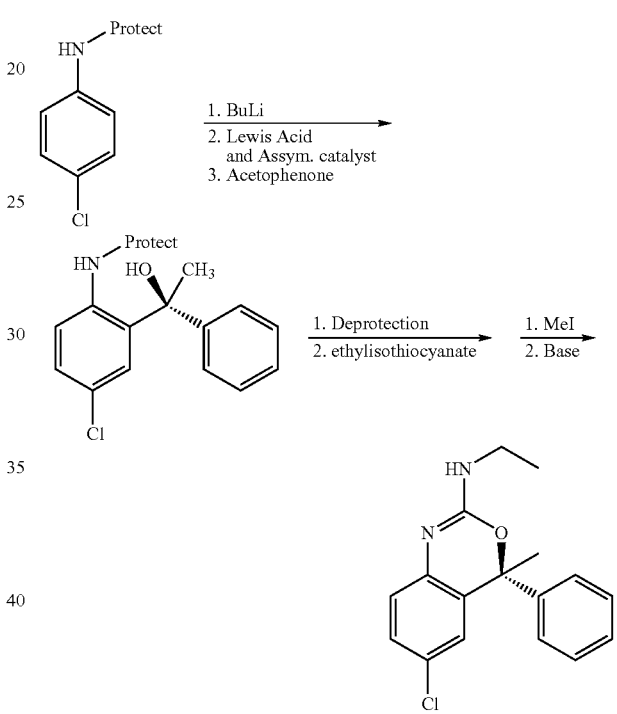

In further embodiments, the etifoxine enantiomer can be prepared by addition of a methyl group to a commercially available 1-amino-4-chlorobenzophenone. Methyl lithium, methyl Grignard or $Me_2Cu$ or $Me_2Zn$ may be added to the benzophenone in the presence of, for instance, an optically active sparteine (or other suitable chiral chelating agent) to give the optically active, 1-amino-4-chloro-7-hydroxy-7-methylbenzhydrol as illustrated in Scheme H. This intermediate could be converted to optically active etifoxine as outlined above.

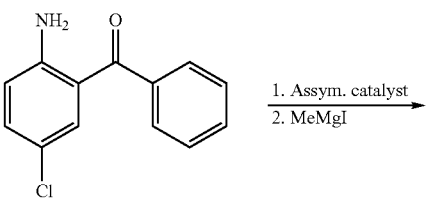

-continued

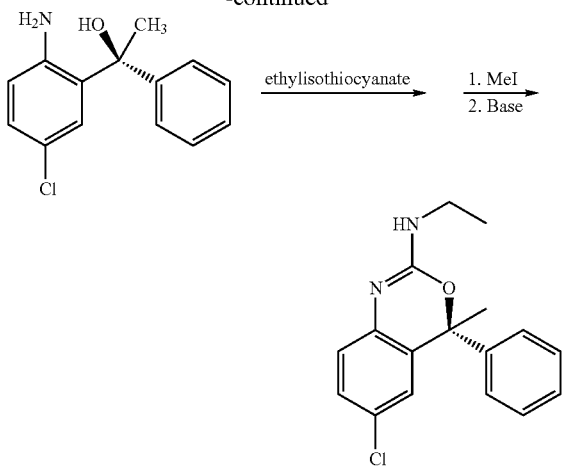

In further embodiments, S-etifoxine can be prepared from S-1-(2-amino-5-chlorophenyl)-1-phenylethanol. Compound A1 can be prepared, for example, by addition of a methyl group to a commercially available (2-amino-5-chlorophenyl)(phenyl) methanone A using a methyl Grignard reagent.

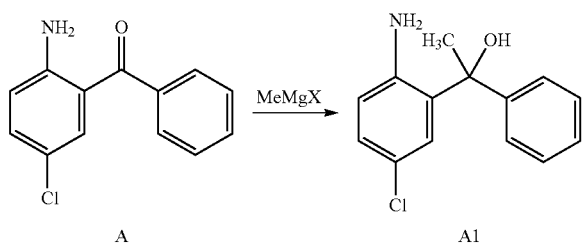

Intermediate A1 can be converted to a dibenzoyl-L-tartaric acid (L-DBTA) salt of 1-(2-amino-5-chlorophenyl)-1-phenylethanol by reaction with dibenzoyl-L-tartaric acid (L-DBTA). The L-DBTA salt can be resolved by, for example, selective precipitation, and the resulting S-A1 can be further converted to S-etifoxine by the reaction sequence described in Examples 1 and 2.

Methods of Treatment, Management and Prevention

In certain embodiments, the pure etifoxine enantiomer provided herein has activity as a GABA modulator. In one embodiment, the enantiomer acts as a modulator of GABA receptor complex and has anxiolytic, anticonvulsant, sedative/hypnotic, and/or anesthetic properties. In one embodiment, the pure etifoxine enantiomer provided herein selectively modulates activity of $GABA_A$ receptors comprising the $\beta_1$ or $\beta_2$ subunit.

In certain embodiments, provided herein are methods of treating or preventing an etifoxine responsive condition comprising administering to a subject in need thereof the pure etifoxine enantiomer.

The pure etifoxine enantiomer provided herein is useful in methods of treating, preventing, ameliorating or managing symptoms associated with anxiety and convulsions. Diseases or disorders associated with anxiety can be categorized in the following: panic disorder without agoraphobia, panic disorder with agoraphobia, agoraphobia without history of panic disorder, specific phobia, social phobia, obsessive compulsive disorder, posttraumatic stress disorder, acute stress disorder, generalized anxiety disorder, anxiety disorder due to a medical condition, substance induced anxiety disorder, anxiety disorder not otherwise specified (NOS). Symptoms associated with anxiety diseases include, but are not limited to, skin blanching, faintness, dilated pupils, elevated blood pressure, dizziness, sweating, sense of fecal or urinary urgency, headache, sinking feeling, chest pain, nausea, palpitations, abdominal distress, dysphoria, muscular tension, distractibility, insomnia, irritability, fatigue and restlessness.

In certain embodiments, the pure etifoxine enantiomer is useful in treatment, prevention, amelioration or management of diseases or disorders, including, but not limited to disorders of central nervous system, such as multiple sclerosis, muscle relaxation in spinal spasticity, cerebral palsy, trigeminal neuralgia, migraine, Alzheimer's disease, pain, drug withdrawal symptoms and convulsive disorders such as epilepsy. In certain embodiments, the pure etifoxine enantiomer is useful in treatment, prevention, amelioration or management of mental disorders, such as anxiety, depression, epilepsy, obsessive compulsive disorders, attention deficit disorder (ADD), attention deficit disorder with hyperactivity (ADHD), sleep disorders, feeding disorders such as anorexia and bulimia, panic attacks, and other mental disorders. In certain embodiments, the pure etifoxine enantiomer is useful in treatment, prevention, amelioration or management of diseases or disorders, including, but not limited to cardiovascular disorders such as hypertension, and gut motility disorders such as irritable bowel syndrome. In certain embodiments, the pure etifoxine enantiomer is useful as an analgesic or antidepressant.

In one embodiment, provided herein is a method for the treatment, prevention, amelioration or management of diseases or disorders, including, but not limited to disorders of central nervous systems or disorders associated with improper GABA receptor activity wherein the method comprises administering S-etifoxine that is substantially free of R-etifoxine.

In certain embodiments, provided herein are methods of using S-etifoxine with reduced sedative effect. Although not intending to be bound by any particular theory of operation, the GABA receptor subunit selectivity described in the examples herein indicates that S-etifoxine has reduced sedating effect. Accordingly, in certain embodiments, S-etifoxine is administered to treat, prevent, ameliorate or manage diseases or disorders, or one or more symptoms thereof, with reduced sedative effect. The sedative effect can be reduced, for instance, compared to a comparable dose of racemic etifoxine or compared to a comparable dose of R-etifoxine. In certain embodiments, the sedative effect of S-etifoxine is less than 90%, 80%, 75%, 70%, 60%, 50%, 40%, 30%, 25%, 20% or 10% of a comparable dose of racemic etifoxine. In certain embodiments, the sedative effect of S-etifoxine is less than 90%, 80%, 75%, 70%, 60%, 50%, 40%, 30%, 25%, 20% or 10% of a comparable dose of R-etifoxine. The sedative effect can be measured according to techniques apparent to those of skill in the art including, for instance, sleep latency, sleep quality, awakenings, sleep length, general well-being and combinations thereof.

Combination Therapy

In certain embodiments, the pure etifoxine enantiomer provided herein is administered in combination with one or more other active ingredients, such as other agents effective for CNS disorders or mental disorders. Such agents include, but are not limited to the following: serotonin receptor (e.g., 5-HT1A) agonists and antagonists; neurokinin receptor antagonists or corticotropin releasing factor receptor (CRF1) antagonists; melatonin receptor agonists; and nicotinic agonists, muscarinic agents, acetylcholinesterase inhibitors and dopamine receptor agonists. In certain embodiments, the other active agents are arylpiperazines, for example buspirone, gepirone, ipsapirone and tondospirone; benzodiazepine derivatives such as alprazolam, bromazepam, camazepam, chlordiazepoxide, clobazam, clorazepate, chotiazepam, cloxazolam, diazepam, ethyl loflazepate, etizolam, fluidazepam, flutazolam, flutoprazepam, halazepam, ketazolam, lorazepam, loxapine, medazepam, metaclazepam, mexazolam, nordazepam, oxazepam, oxazolam, pinazepam, prazepam and tofisopam; carbamates such as cyclarbamate, emylcamate, hydroxyphenamate, meprobamate, phenprobamate and tybamate; and others such as alpidem, benzoctamine, captodiamine, chlormezanone, flesinoxan, fluoresone, glutamic acid, hydroxyzine, lesopitron, mecloralurea, mephenoxalone, mirtazepine, oxanamide, phenaglycodol, suriclone and zatosetron.

In certain embodiments, the other active agent is fluoxetine (Prozac®), paroxetine (Paxil®), sertraline (Zoloft®), citalopram (Celexa®) orfluvoxamine (Luvox®), venlafaxine (Effexor®), mirtazapine (Remeron®), nefazodone (Serzone®), trazodone (Desyrel®), venlafaxine (Effexor®), bupropion (Wellbutrin®), lithium (Eskalith, Lithobid®), valproate (Depakene®, Depakote®) carbamazepine (Epitol, Tegretol®), neurontin (Gabapentin®), lamictal (Lamotrigine®), ziprasidone (Geodon®), risperidone (Risperdal®), quetiapine (Seroquel®), phenelzine (Nardil®), tranylcypromine (Parnate®), amitriptyline (Elavil®), protriptyline (Vivactil®), desipramine (Norpramin®), nortriptyline (Aventyl®, Pamelor®), trimipramine (Surmontil®), perphenazine (Triavil®), maprotiline (Ludiomil®), mirtazapine (Remeron®), methylphenidate (Ritalin®) or dextroamphetamine (Dexedrine®).

In certain embodiments, the other active agent is an antidepressant, such as a tricyclic antidepressant ("TCA"), a selective serotonin reuptake inhibitor ("SSRI"), a serotonin and noradrenaline reuptake inhibitor ("SNRI"), a dopamine reuptake inhibitor ("DRI"), a noradrenaline reuptake inhibitor ("NRI"), a dopamine and noradrenaline reuptake inhibitor ("DNRI"), a monoamine oxidase inhibitor ("MAOI"), an alpha-2-receptor blocker or another antidepressant.

Exemplary TCAs include, but are not limited to, amitriptyline (Elavil®), amoxapine (Asendin®), clomipramine (Anafranil®), desipramine (Norpramin®), doxepin (Adapin®, Sinequan®), imipramine (Tofranil®), maprotiline (Ludiomil®), nortriptyline (Aventyl®, Pamelor®), protriptyline (Vivactil®) and trimipramine (Surmontil®).

Exemplary SSRIs include, but are not limited to, sertraline (Zoloft®), sertraline metabolite demethylsertraline, fluoxetine (Prozac®), norfluoxetine (fluoxetine desmethyl metabolite), fluvoxamine (Luvox®), paroxetine (Seroxat®, Paxil®) and its alternative formulation, Paxil-CR®, citalopram (Celexa®), citalopram metabolite desmethylcitalopram, escitalopram (Lexapro®), d,l-fenfluramine (Pondimin®), femoxetine, ifoxetine, cyanodothiepin, litoxetine, cericlamine and dapoxetine.

Exemplary NRIs include, but are not limited to, reboxetine (Edronax®) and all isomers of reboxetine, i.e., (R/R,S/S,R/S,S/R), desipramine (Norpramin®), maprotiline (Ludiomil®), lofepramine (Gamanil®), oxaprotiline, fezolamine, atomoxetine (Strattera®), nomifensine (Merital®), viloxazine (Vivalan®), or mianserin (Bolvidon®).

Exemplary SNRIs include, but are not limited to, venlafaxine (Effexor®), venlafaxine metabolite O-desmethylvenlafaxine, clomipramine (Anafranil®), clomipramine metabolite desmethylclomipramine, duloxetine (Cymbalta®), milnacipran, imipramine (Tofranil® or Janimine®) and nefazaodone (Serzone®).

Exemplary MAOIs include, but are not limited to, phenelzine (Nardil®), tranylcypromine (Parnate®), isocarboxazid (Marplan®) and selegiline (Emsam®, Eldepryl®).

Exemplary alpha-2-receptor blockers include, but are not limited to, mirtazapine (Remeron®, Remeron Soltab®).

Other useful antidepressants include buprorion (Wellbutrin®, Zyban®), buproprion metabolite hydroxybuproprion and trazodone (Desyrel®).

In one embodiment, in the methods provided herein, a pure etifoxine enantiomer is used as an unsolvated or a free compound. In another embodiment, in the methods provided herein, a pure etifoxine enantiomer is used as a salt, such as a hydrochloride salt. In another embodiment, in the methods provided herein, a pure etifoxine enantiomer used as a solvate.

Pharmaceutical Compositions and Dosage Forms

Pharmaceutical compositions and dosage forms for use in the methods provided herein comprise the pure etifoxine enantiomer or a pharmaceutically acceptable salt, solvate, hydrate or prodrug thereof in a pharmaceutical carrier, excipient or diluent and in amounts that are useful in the methods provided herein. Such compositions can be used in methods that include, but are not limited to treatment, prevention, amelioration or management of symptoms of conditions associated with anxiety, convulsions, disorders of central nervous systems, such as multiple sclerosis, muscle relaxation in spinal spasticity, cerebral palsy, trigeminal neuralgia, pain and drug withdrawal symptoms, other nervous disorders, cardiovascular disorders such as hypertension, and gut motility disorders such as irritable bowel syndrome.

In one embodiment, in the compositions provided herein, the pure etifoxine enantiomer is used as an unsolvated or a free compound. In another embodiment, in the compositions provided herein, the pure etifoxine enantiomer is used as a salt, such as a hydrochloride salt. In another embodiment, in the compositions provided herein, the pure etifoxine enantiomer used as a solvate.

In certain embodiments, the compositions provided herein comprise from about 1% to about 99%, from about 5% to about 95%, from about 10% to about 90%, from about 15% to about 85%, from about 20% to about 80%, from about 25% to about 75%, from about 30% to about 70%, from about 40% to about 60% of the pure etifoxine enantiomer or a pharmaceutically acceptable salt, solvate, hydrate or prodrug thereof. In certain embodiments, the compositions comprise 99%, 95%, 90%, 85%, 80%, 75%, 70%, 60%, 55%, 50%, 45%, 40%, 35%, 30%, 25%, 20%, 15%, 10%, 7%, 5%, 3%, 2% or 1% of the pure etifoxine enantiomer or a pharmaceutically acceptable salt, solvate, hydrate or prodrug thereof. The composition can further comprise other active ingredients and pharmaceutically acceptable carrier, excipient or diluent.

A pharmaceutical composition provided herein is formulated to be compatible with its intended route of administration. Examples of routes of administration include, but are not limited to, parenteral, intravenous, intradermal, subcutaneous, intramuscular, oral, mucosal, buccal, sublingual, inhalation, intranasal, transdermal, topical, intra-tumoral, intra-synovial and rectal administration. In a specific embodiment, the composition is formulated in accordance with routine procedures as a pharmaceutical composition adapted for intravenous, subcutaneous, intramuscular, oral, intranasal or topical administration to human beings.

Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

In certain embodiments, the pure enantiomer provided herein is formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. Typically the formulation are prepared using techniques and procedures well known in the art (see, e.g., Ansel Introduction to Pharmaceutical Dosage Forms and Drug Delivery Systems, Eighth Edition 2004).

In certain compositions, the effective concentration of an enantiomer provided herein is mixed with a pharmaceutical acceptable carrier or vehicle. The term "carrier" refers to a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Examples of suitable pharmaceutical carriers are described in "Remington's Pharmaceutical Sciences" by E. W. Martin.

Typical pharmaceutical compositions and dosage forms comprise one or more excipients. Suitable excipients are well-known to those skilled in the art of pharmacy, and non-limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a patient and the specific active ingredients in the dosage form. The composition or single unit dosage form, if desired, can also contain minor amounts of wetting or emulsifying agents, or pH buffering agents.

In certain embodiments, the concentration of a pure enantiomer in the compositions is effective for delivery of an amount, upon administration, that treats, prevents, or ameliorates one or more of the symptoms of conditions associated with anxiety, convulsions, disorders of central nervous systems, such as multiple sclerosis, muscle relaxation in spinal spasticity, cerebral palsy, trigeminal neuralgia, pain and drug withdrawal symptoms, other nervous disorders. In certain embodiment, the concentration of a pure enantiomer in the compositions is effective for delivery of an amount, upon administration, that treats, prevents, or ameliorates one or more of the symptoms of conditions associated with cardiovascular disorders such as hypertension, and gut motility disorders such as irritable bowel syndrome.

Typically, the compositions are formulated for single dosage administration. To formulate a composition, the weight fraction of an enantiomer provided herein is dissolved, suspended, dispersed or otherwise mixed in a selected vehicle at an effective concentration such that the treated condition is relieved or ameliorated. Pharmaceutical carriers or vehicles suitable for administration of the enantiomer provided herein include any such carriers known to those skilled in the art to be suitable for the particular mode of administration.

In addition, a pure enantiomer provided herein may be formulated as the sole pharmaceutically active ingredient in the composition or may be combined with other active ingredients. Thus, provided herein are single unit dosage forms of the pure enantiomer of etifoxine and a carrier, excipient or diluent.

Liposomal suspensions, including tissue-targeted liposomes, may also be suitable as pharmaceutically acceptable carriers. These may be prepared according to methods known to those skilled in the art. For example, liposome formulations may be prepared as described in U.S. Pat. Nos. 4,522,811 and 5,571,534. Briefly, liposomes such as multilamellar vesicles (MLV's) may be formed by drying down egg phosphatidyl choline and brain phosphatidyl serine (7:3 molar ratio) on the inside of a flask. A solution of a conjugate provided herein in phosphate buffered saline lacking divalent cations (PBS) is added and the flask shaken until the lipid film is dispersed. The resulting vesicles are washed to remove unencapsulated enantiomer, pelleted by centrifugation, and then resuspended in PBS.

A pure enantiomer is included in the pharmaceutically acceptable carrier in an amount sufficient to exert desired effect in the patient treated. The therapeutically effective concentration may be determined empirically by testing the enantiomer in in vitro and in vivo systems known to one of skill in the art and then extrapolated therefrom for dosages for humans.

The concentration of the enantiomer provided herein in the pharmaceutical composition will depend on absorption, inactivation and excretion rates of the enantiomer, the dosage schedule, and amount administered as well as other factors known to those of skill in the art.

The composition, shape, and type of dosage forms of the invention will typically vary depending on their use. For example, a dosage form used in the acute treatment of a disease may comprise larger amounts of one or more of the active ingredients than a dosage form used in the chronic treatment of the same disease. Similarly, a parenteral dosage form may comprise smaller amounts of one or more of the active ingredients than an oral dosage form used to treat the same disease. These and other ways in which specific dosage forms encompassed by this invention will vary from one another will be readily apparent to those skilled in the art. See, e.g., *Remington: The Science and Practice of Pharmacy,* 21st ed., (2005).

Typically a therapeutically effective dosage should produce a serum concentration of active ingredient of from about 0.1 ng/ml to about 50-100 µg/ml. Pharmaceutical dosage unit forms are prepared to provide from about 1 mg to about 2000 mg, from about 4 mg to about 1750 mg, from about 6 mg to about 1500 mg, from about 8 mg to about 1200 mg, from about 10 mg to about 1000 mg, from about 13 mg to about 800 mg, from about 15 mg to about 500 mg, from about 25 to about 400 mg, from about 50 up to about 200 mg, from about 75 up to about 175 mg or from about 100 up to about 150 mg of the essential active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the compositions provided herein.

In certain embodiments, the compound or composition provided herein can be administered as a single once-a-day dose or preferably as divided doses throughout a day. In some embodiments, the daily dose is administered twice daily in equally divided doses. In other embodiments, the daily dose is administered three times per day. In particular embodiments, the daily dose is administered three times per day in equally divided doses. In some embodiments, the daily dose is administered three times per day in three divided doses and each dose comprises the active compound in an amount between about 1 mg to about 2000 mg, from about 4 mg to about 1750 mg, from about 6 mg to about 1500 mg, from about 8 mg to about 1200 mg, from about 10 mg to about 1000 mg, from about 13 mg to about 800 mg, from about 15 mg to about 500 mg, from about 25 to about 400 mg, from about 50 up to about 200 mg, from about 75 up to about 175 mg or from about 100 up to about 150 mg. Alternatively, each dose comprises the active compound in an amount in the range 1-5 mg/kg, 1-4 mg/kg or 1-3 mg/kg of body weight.

Different therapeutically effective amounts may be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the co-complexes of the invention are also encompassed by the above described dosage amounts and dose frequency schedules. Further, when a patient is administered multiple dosages of a the compound provided herein, not all of the dosages need be the same. For example, the dosage administered to the patient may be increased to improve the prophylactic or therapeutic effect of the compound or it may be decreased to reduce one or more side effects that a particular patient is experiencing.

Thus, effective concentrations or amount of a pure enantiomer or its pharmaceutically acceptable salt, solvate, hydrate or prodrug is mixed with a suitable pharmaceutical carrier, excipient, diluent or vehicle for systemic, topical or local administration to form the pharmaceutical composition. In certain embodiments, the pure etifoxine enantiomer or its pharmaceutically acceptable salt, solvate, hydrate or prodrug is included in an amount effective for treating, preventing or managing anxiety, convulsions, disorders of central nervous systems, such as multiple sclerosis, muscle relaxation in spinal spasticity, cerebral palsy, trigeminal neuralgia, pain and drug withdrawal symptoms and other nervous disorders. In certain embodiments, the pure etifoxine enantiomer or its pharmaceutically acceptable salt, solvate, hydrate or prodrug is included in an amount effective for treating, preventing or managing anxiety and convulsions.

The compositions are intended to be administered by a suitable route, including orally, parenterally, rectally, topically and locally. The enantiomer provided herein or a pharmaceutically acceptable salt, solvate, hydrate or prodrug thereof is typically formulated and administered in unit-dosage forms such as tablets, capsules, pills, powders, granules, sterile parenteral solutions or suspensions, and oral solutions or suspensions, and oil-water emulsions comprising suitable quantities of the active ingredient or multiple-dosage forms. Unit-dose forms as used herein refer to physically discrete units suitable for human and animal subjects and packaged individually as is known in the art. Each unit-dose comprises a predetermined quantity of the therapeutically active enantiomer sufficient to produce the desired therapeutic effect, in association with the required pharmaceutical carrier, excipient, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, a multiple dose form is a multiple of unit-doses which are not segregated in packaging.

Lactose-free compositions provided herein can comprise excipients that are well known in the art and are listed, for example, in the *U.S. Pharmacopeia* (USP) 25-NF20 (2002). In general, lactose-free compositions comprise active ingredients, a binder/filler, and a lubricant in pharmaceutically compatible and pharmaceutically acceptable amounts. Particular lactose-free dosage forms comprise active ingredients, microcrystalline cellulose, pre-gelatinized starch, and magnesium stearate.

Further provided are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice,* 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms provided herein can be prepared using anhydrous or low moisture containing ingredients and low moisture or low humidity conditions.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

a. Compositions for Oral Administration

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art. Such dosage forms comprise predetermined amounts of active ingredients, and may be prepared by methods of pharmacy well known to those skilled in the art. See generally, *Remington's Pharmaceutical Sciences,* 21st ed., (2005).

In certain embodiments, the formulations are solid dosage forms, preferably capsules or tablets. The tablets, pills, capsules, troches and the like can comprise any of the following ingredients, or conjugates of a similar nature: a binder; a filler, a diluent; a disintegrating agent; a lubricant; a glidant; a sweetening agent; and a flavoring agent. Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Disintegrants are used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, preferably from about 1 to about 5 weight percent of disintegrant.

Disintegrants that can be used in pharmaceutical compositions and dosage forms provided herein include, but are not limited to, agar-agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and mixtures thereof.

Lubricants that can be used in pharmaceutical compositions and dosage forms provided herein include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

For oral administration, the composition can be formulated as enterically coated tablets, sugar-coated tablets, film-coated tablets or multiple compressed tablets. Enteric coating tablets protect the active ingredient from the acidic environment of the stomach. Sugar-coated tablets are compressed tablets to which different layers of pharmaceutically acceptable substances are applied. Film-coated tablets are compressed tablets which have been coated with a polymer or other suitable coating. Multiple compressed tablets are compressed tablets made by more than one compression cycle utilizing the pharmaceutically acceptable substances previously mentioned. Coloring agents may also be used in the above dosage forms. Flavoring and sweetening agents are used in compressed tablets, sugar-coated, multiple compressed and chewable tablets. Flavoring and sweetening agents are especially useful in the formation of chewable tablets and lozenges. The composition may also be formulated in combination with an antacid or other such ingredient.

When the dosage unit form is a capsule, it can comprise, in addition to material of the above type, a liquid carrier such as a fatty oil. In a gelatin capsule, the solution or suspension comprising an active ingredient, in for example propylene carbonate, vegetable oils or triglycerides, is preferably encapsulated in the capsule. The active ingredient can also be mixed with other active materials which do not impair the desired action, or with materials that supplement the desired action, such as antacids, H2 blockers, and diuretics. Higher concentrations, up to about 98% by weight of the active ingredient may be included.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative.

An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic add, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia.

Diluents include lactose and sucrose. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation. The pharmaceutical compositions comprising active ingredients in micellar form can be prepared as described in U.S. Pat. No. 6,350,458. Such pharmaceutical compositions are particularly effective in oral, nasal and buccal applications.

In certain embodiments, the enantiomer provided herein can be formulated in oral capsules or tablets comprising about 15 mg, about 25 mg, about 40 mg, about 50 mg, about 75 mg, about 100 mg, about 120 mg, about 150 mg, about 175 mg, about 200 mg, about 250 mg or about 300 mg of the active ingredient.

b. Controlled Release Dosage Form

Active ingredients provided herein can be administered by controlled release means or by delivery devices that are well known to those of ordinary skill in the art. The controlled release can be any controlled release known to those of skill including, for example, delayed release, sustained release and pulsed release. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, 5,639,480, 5,733,566, 5,739,108, 5,891,474, 5,922,356, 5,972,891, 5,980,945, 5,993,855, 6,045,830, 6,087,324, 6,113,943, 6,197,350, 6,248,363, 6,264,970, 6,267,981, 6,376,461, 6,419,961, 6,589,548, 6,613,358, 6,699,500 and 6,740,634, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients provided herein. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

In certain embodiments, the agent may be administered using intravenous infusion, an implantable osmotic pump, a transdermal patch, liposomes, or other modes of administration. In one embodiment, a pump may be used (see, Sefton, *CRC Crit. Ref. Biomed. Eng.* 14:201 (1987); Buchwald et al., Surgery 88:507 (1980); Saudek et al., *N. Engl. J. Med.* 321: 574 (1989)). In another embodiment, polymeric materials can be used. In yet another embodiment, a controlled release system can be placed in a subject at an appropriate site determined by a practitioner of skill, i.e., thus requiring only a fraction of the systemic dose (see, e.g., Goodson, *Medical Applications of Controlled Release*, vol. 2, pp. 115-138 (1984)). Other controlled release systems are discussed in the review by Langer (*Science* 249:1527-1533 (1990)). The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient in such parenteral compositions is highly dependent on the specific nature thereof, as well as the needs of the subject.

c. Parenteral Administration

Parenteral administration, generally characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. Suitable excipients are, for example, water, saline, dextrose, glycerol or ethanol. In addition, if desired, the pharmaceutical compositions to be administered may also comprise minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers, excipient or diluents used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of an active ingredient is adjusted so that an injection provides an effective amount to produce the desired pharmacological effect. The exact dose depends on the age, weight and condition of the patient or animal as is known in the art.

The unit-dose parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution comprising an active ingredient is an effective mode of administration. Another embodiment is a sterile aqueous or oily solution or suspension comprising an active material injected as necessary to produce the desired pharmacological effect.

Injectables are designed for local and systemic administration. Typically a therapeutically effective dosage is formulated to contain a concentration of at least about 0.1% w/w up to about 90% w/w or more, preferably more than 1% w/w of an active ingredient to the treated tissue(s). The active ingredient may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

The active enantiomer may be suspended in micronized or other suitable form or may be derivatized to produce a more soluble active product or to produce a prodrug. The form of the resulting mixture depends upon a number of factors, including the intended mode of administration and the solubility of an active enantiomer in the selected carrier or vehicle. The effective concentration is sufficient for ameliorating the symptoms of the condition and may be empirically determined.

d. Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving the active ingredient, or a pharmaceutically acceptable salt, solvate, hydrate or prodrug thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, typically, about neutral pH. Subsequent sterile filtration of the solution followed by lyophilization under standard conditions known to those of skill in the art provides the desired formulation. Generally, the resulting solution will be apportioned into vials for lyophilization. Each vial will contain a single dosage (10-1000 mg, preferably 100-500 mg) or multiple dosages of the pure etifoxine enantiomer. The lyophilized powder can be stored under appropriate conditions, such as at about 4° C. to room temperature.

Reconstitution of this lyophilized powder with water for injection provides a formulation for use in parenteral administration. For reconstitution, about 1-50 mg, preferably 5-35 mg, more preferably about 9-30 mg of lyophilized powder, is added per mL of sterile water or other suitable carrier. The precise amount depends upon the active enantiomer. Such amount can be empirically determined.

e. Topical Administration

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The pure etifoxine enantiomer may be formulated for local or topical application, such as for topical application to the skin and mucous membranes, in the form of gels, creams, and lotions. Topical administration is contemplated for transdermal delivery and also for mucosal administration, or for inhalation therapies. In certain embodiments, the pure etifoxine enantiomer is formulated as gels comprising about 15 mg, about 20 mg, about 25 mg, about 30 mg, about 40 mg, about 50 mg, about 75 mg, about 90 mg, about 100 mg or about 150 mg of the pure etifoxine enantiomer.

f. Compositions for Other Routes of Administration

Other routes of administration, such as topical application, transdermal patches, and rectal administration are also contemplated herein. For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is about 2 to 3 gm.

Tablets and capsules for rectal administration are manufactured using the same pharmaceutically acceptable substance and by the same methods as for formulations for oral administration.

Also provided are transdermal, topical, and mucosal dosage forms. Transdermal, topical, and mucosal dosage forms of the invention include, but are not limited to, ophthalmic solutions, sprays, aerosols, creams, lotions, ointments, gels, solutions, emulsions, suspensions, or other forms known to one of skill in the art. See, e.g., *Remington: The Science and Practice of Pharmacy*, 21st ed., (2005); Introduction to Pharmaceutical Dosage Forms, 4th ed., Lea & Febiger, Philadelphia (1985) and Ansel Introduction to Pharmaceutical Dosage Forms and Drug Delivery Systems, Eighth Edition 2004). Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form lotions, tinctures, creams, emulsions, gels or ointments, which are non-toxic and pharmaceutically acceptable. Moisturizers or humectants can also be added to pharmaceutical compositions and dosage forms if desired. Examples of such additional ingredients are well known in the art. See, e.g., Remington's Pharmaceutical Sciences, 16th and 18th eds., Mack Publishing, Easton Pa. (1980 & 1990).

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

Articles of Manufacture

The pure etifoxine enantiomer for use in the methods provided herein can be packaged as an article of manufacture using packaging materials well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, and any packaging material suitable for a selected formulation and intended mode of administration and treatment.

Kits

Provided herein, are kits which, when used by the medical practitioner, can simplify the administration of appropriate amounts of active ingredients to a patient. In certain embodiments, the kit provided herein includes a container and a dosage form of the pure etifoxine enantiomer or a pharmaceutically acceptable salt, solvate, hydrate or prodrug thereof.

In certain embodiments, the pure etifoxine enantiomer provided herein is administered in combination with other therapeutic agents as described herein. The other therapeutic agents may or may not be administered to a patient at the same time or by the same route of administration. In certain embodiments, the kit includes a container comprising a dosage form of the pure etifoxine enantiomer or a pharmaceutically acceptable salt, solvate, hydrate or prodrug thereof and a container comprising one or more other therapeutic agent(s) described elsewhere herein. Such other therapeutic agents include, but are not limited to Arylpiperazines, for example Buspirone, Gepirone, Ipsapirone and Tondospirone; Benzodiazepine derivatives such as Alprazolam, Bromazepam, Camazepam, Chlordiazepoxide, Clobazam, Clorazepate, Chotiazepam, Cloxazolam, Diazepam, Ethyl Loflazepate, Etizolam, Fluidazepam, Flutazolam, Flutoprazepam, Halazepam, Ketazolam, Lorazepam, Loxapine, Medazepam, Metaclazepam, Mexazolam, Nordazepam, Oxazepam, Oxazolam, Pinazepam, Prazepam and Tofisopam; Carbamates such as Cyclarbamate, Emylcamate, Hydroxyphenamate, Meprobamate, Phenprobamate and Tybamate; and others such as Alpidem, Benzoctamine, Captodiamine, Chlormezanone, Flesinoxan, Fluoresone, Glutamic Acid, Hydroxyzine, Lesopitron, Mecloralurea, Mephenoxalone, Mirtazepine, Oxanamide, Phenaglycodol, Suriclone and Zatosetron.

In certain embodiments, the other therapeutic agent is fluoxetine (Prozac®), paroxetine (Paxil®), sertraline (Zoloft®), citalopram (Celexa®) orfluvoxamine (Luvox®), venlafaxine (Effexor®), mirtazapine (Remeron®), nefazodone (Serzone®), trazodone (Desyrel®), venlafaxine (Effexor®), bupropion (Wellbutrin®), lithium (Eskalith, Lithobid®), valproate (Depakene®, Depakote®) carbamazepine (Epitol, Tegretol®), neurontin (Gabapentin®), lamictal (Lamotrigine®), ziprasidone (Geodon®), risperidone (Risperdal®), quetiapine (Seroquel®), phenelzine (Nardil®), tranylcypromine (Parnate®), amitriptyline (Elavil®), protriptyline (Vivactil®), desipramine (Norpramin®), nortriptyline (Aventyl®, Pamelor®), trimipramine (Surmontil®), perphenazine (Triavil®), maprotiline (Ludiomil®), mirtazapine (Remeron®), methylphenidate (Ritalin®) or dextroamphetamine (Dexedrine®).

Kits provided herein can further include devices that are used to administer the active ingredients. Examples of such devices include, but are not limited to, syringes, needle-less injectors drip bags, patches, and inhalers.

Kits provided herein can further include pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Evaluation of Biological Activity

Standard physiological, pharmacological and biochemical procedures are available are known to one of skill in the art to test the efficacy of the pure enantiomer in the methods provided herein. In vitro and in vivo assays that can be used to evaluate biological activity contemplated herein.

For example, anticonvulsant activity of the compounds can be determined by methods described in U.S. Pat. No. 3,725,404. GABA modulating activity of the pure etifoxine enantiomer can be tested by their ability to modulate the GABA-evoked chloride currents in *Xenopus* oocytes. The chloride currents can be monitored using two voltage electrode clamp technique. Such assays can be performed by methods known to one of skill in the art, for example, see, Hamon et al., 2003, *Neuropharmacology*, 45: 293-303 and Whittemore et al., 1996, *Mol Pharmacol* 50: 1364-1375.

EXAMPLES

High performance liquid chromatography (HPLC) experiments were performed using CHIRALCEL® OF column from Diacel Chemical Industries, Ltd.

Example 1

Preparation of L-DBTA salt of 1-(2-amino-5-chlorophenyl)-1-phenylethanol

Step 1:

A 250 mL round-bottomed-flask equipped with a magnetic stir bar was charged with 1-(2-amino-5-chlorophenyl)-1-phenylethanol, (10.30 g, 41.6 mmol), dibenzoyl-L-tartaric acid (L-DBTA, 7.45 g, 20.8 mmol) and EtOAc (83 mL). The resulting solution was warmed to 55° C. and heptane (40 mL) was added. The resulting solution was seeded and then warmed to 70° C. Additional heptane (43 mL) was added and the temperature was held at 70° C. for 15 min providing a seed bed. The suspension was allowed to cool to 30° C. to provide a thick suspension. The suspension was again warmed to 70° C. and the heavy suspension remained. The suspension was allowed to cool over 3 h to rt. There resulting salt was then collected on a frit, rinsed with 25 mL of 40% EtOAc/heptane, and air dried to provide 8.60 g (34.1%, 68.2% of theory for single enantiomer) of a white solid. The material was determined to be 80% ee by chiral HPLC analysis. The mother liquor was 45% ee of the opposite enantiomer. $^1$H NMR confirmed that the ratio of L-DBTA:aniline was 1:1.

A 250 mL round-bottomed-flask equipped with a magnetic stir bar was charged with the L-DBTA salt of 1-(2-amino-5-chlorophenyl)-1-phenylethanol, (6.40 g, 80% ee), EtOAc (50 mL) and warmed to provide a solution (35° C.). Heptane (50 mL) was added and the solution was seeded and warmed to 70° C. The slight suspension was warmed to 70° C. then allowed to cool to 25° C. The resulting heavy white suspension was warmed to 70° C. and allowed to cool over 2 h to rt. The solids were collected on a frit, rinsed with 30 mL of 33% EtOAc/heptane and air dried to provide 4.02 g (63% recovery) of the L-DBTA salt with 96% ee.

The L-DBTA salt can be convered to a free base for use in further reactions by methods known to one of skill in the art, for example, by using a base such as diethylamine or triethylamine.

Example 2

Preparation of S-Etifoxine

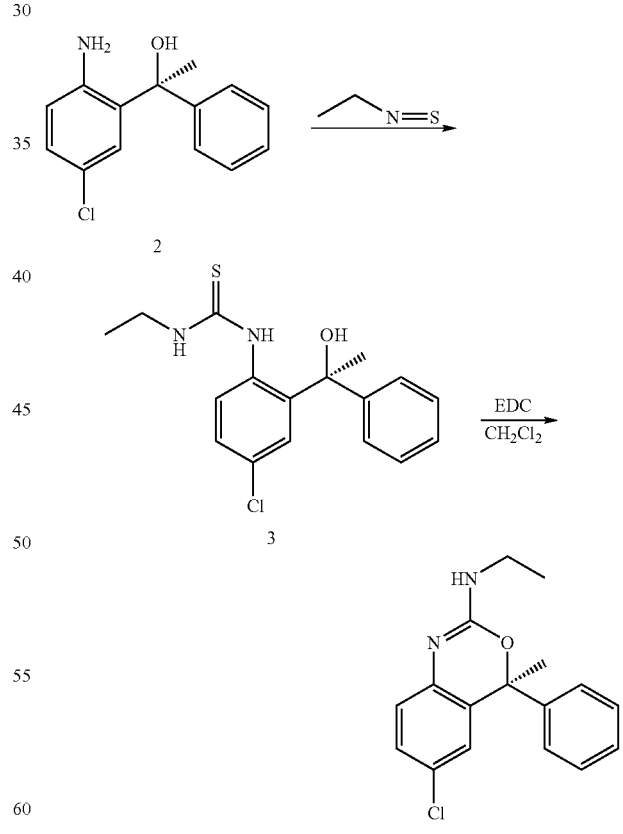

Step 1: Preparation of Thiourea 3.

A 50-L, 3-necked round bottom flask equipped with a mechanical stirrer, thermocouple, $N_2$ by demand inlet/outlet and a heating mantle, was charged with toluene (12 L) and heptane (5 L) followed by 2293 g (9.26 moles) of 2. To the stirring mixture was added 1216 mL (13.9 moles, 1.5 eq) of N-ethylisothiocyanate. No significant exotherm was observed. The mixture was warmed and stirred at 40-45° C. for 4 h after which time, HPLC analysis showed ~10% starting material. The reaction was allowed to cool and stir at ambient temperature overnight (17 h), after which time HPLC analysis showed ~2% starting material. The reaction mixture was concentrated under reduced pressure to provide a thick slurry. Additional heptane (2 L) was added to the slurry. The mixture was swirled on the rotary evaporator at 45° C. for 10 minutes then allowed to cool to room temperature. The resulting slurry was cooled to 5-10° C. and filtered and the filter cake was rinsed with 2×2 L of cold toluene/heptane (1:1). The product was dried in a vacuum oven for 18 h at 45-50° C. to give 2713 g (87.5%) of 3a as a white solid.

Step 2: Preparation of S-Etifoxine Oxalate Salt

Optically pure peak 2 thiourea 3 (41.1 g, 123 mmol), 1-ethyl-3-[3-dimethylaminopropyl]carbodiimide hydrochloride (EDC) (28.2 g, 147 mmol) and $CH_2Cl_2$ (400 mL) were combined in a 1 L round-bottomed-flask and stirred at rt for 47 h. The mixture was concentrated under vacuum to a slurry and then diluted with EtOAc (100 mL) and filtered. The solids were rinsed with EtOAc (200 mL). The filtrate was extracted with water (2×100 mL), brine (75 mL) and dried ($Na_2SO_4$), filtered and concentrated to provide S-etifoxine free base. A portion of the free base (8.2 g) was dissolved in acetone (24 mL) and warmed to 40° C. To the stirred solution was added oxalic acid (2.4 g) to provide a clear colorless solution. Heptane (22 mL) was added slowly to provide a hazy mixture which was seeded and allowed to cool to rt. A large crop of solids formed. After 2 h at rt, the solids were collected on a frit and dried in a vacuum oven at 30° C. to provide 7.08 g of the S-etifoxine 4 oxalate salt.

Example 3

HPLC Separation of Pure Enantiomers of Etifoxine

The separation of 0.73 g of racemic etifoxine was achieved by chiral HPLC using a CHIRALCEL® OF (Daicel), 4.6 mm×250 mm column. The separation was carried out with $CO_2$:MeOH (90:10 by volume) as liquid phase. The flow rate was set at 2 ml/min at 25° C. The compounds were detected at 254 nm.

Figure 2A:
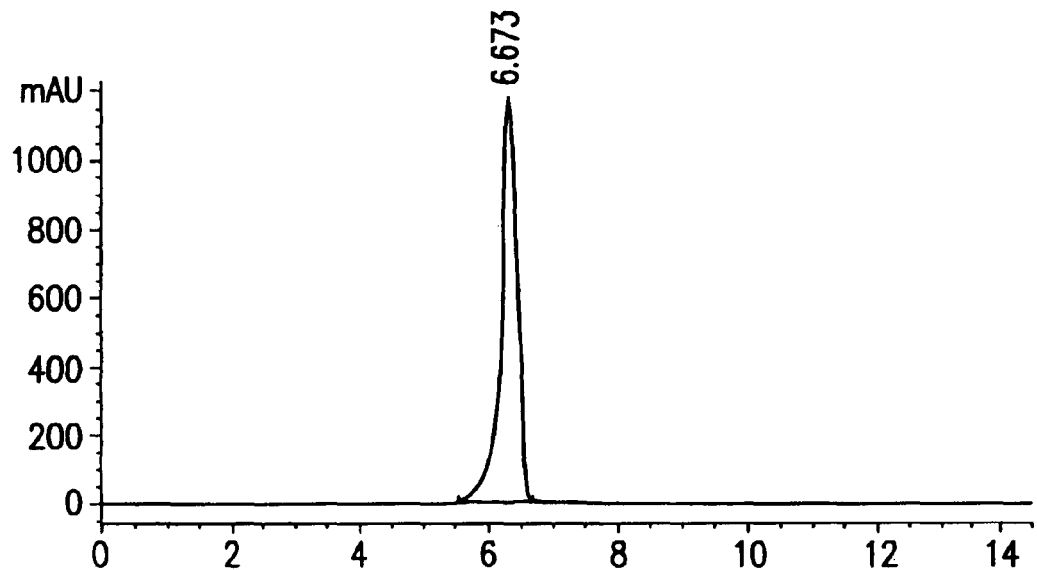
FIG. 2A provides an HPLC trace of the enantiomer corresponding to isolated peak 1.
Figure 2B:
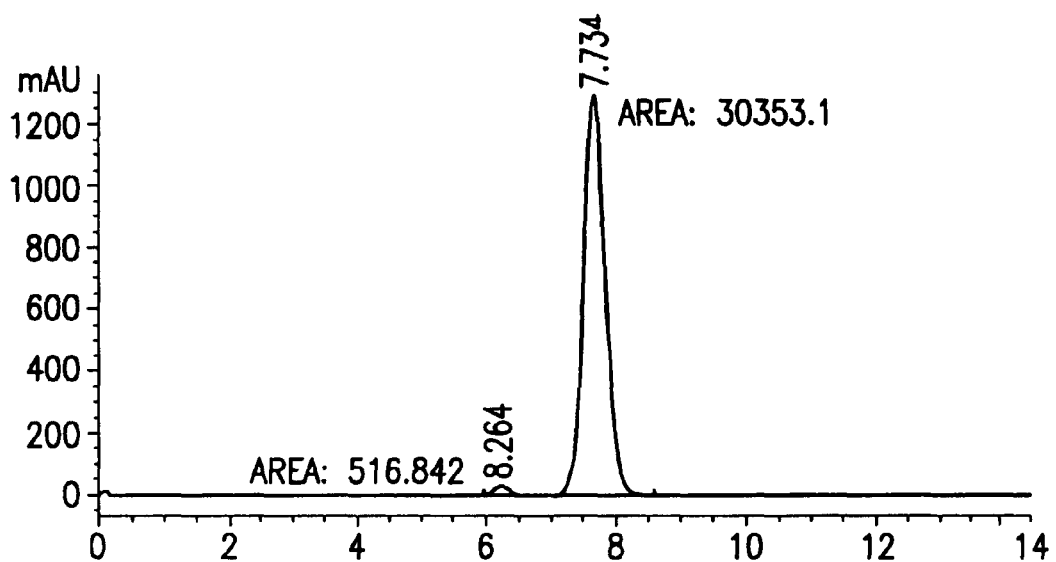
FIG. 2B provides an HPLC trace of the enantiomer corresponding to isolated peak 2.

As shown in FIG. 1, the two enantiomers were resolved as separated peaks with distinct retention times for each peak. The enantiomer corresponding to peak 1 had a retention time of 6.49 minutes and the enantiomer corresponding to peak 2 had a retention time of 8.82 minutes. The yield of the two enantiomers was 0.32 g for the enantiomer corresponding to peak 1 and 0.30 g for the enantiomer corresponding to peak 2. The two enantiomers were obtained with an enantiomeric excess value of >99% for peak 1 and 96.6% for peak 2, respectively. The HPLC traces of the isolated enantiomers are provided in FIGS. 2A and 2B.

Example 4

Preparation of the Etifoxine Peak 1 Derivative

To a solution of enantiomerically pure etifoxine identified as peak 1 (0.16 mmol, 48 mgs) in THF (2 mL) was added (S)-(+)-1-(1-naphtyl)-ethyl isocyanate (0.16 mmol, 28 μL). The mixture was stirred overnight at room temperature. The solvent was then removed under reduced pressure to yield a white solid. This solid was recrystallized from acetonitrile to provide small needles.

Figure 8:
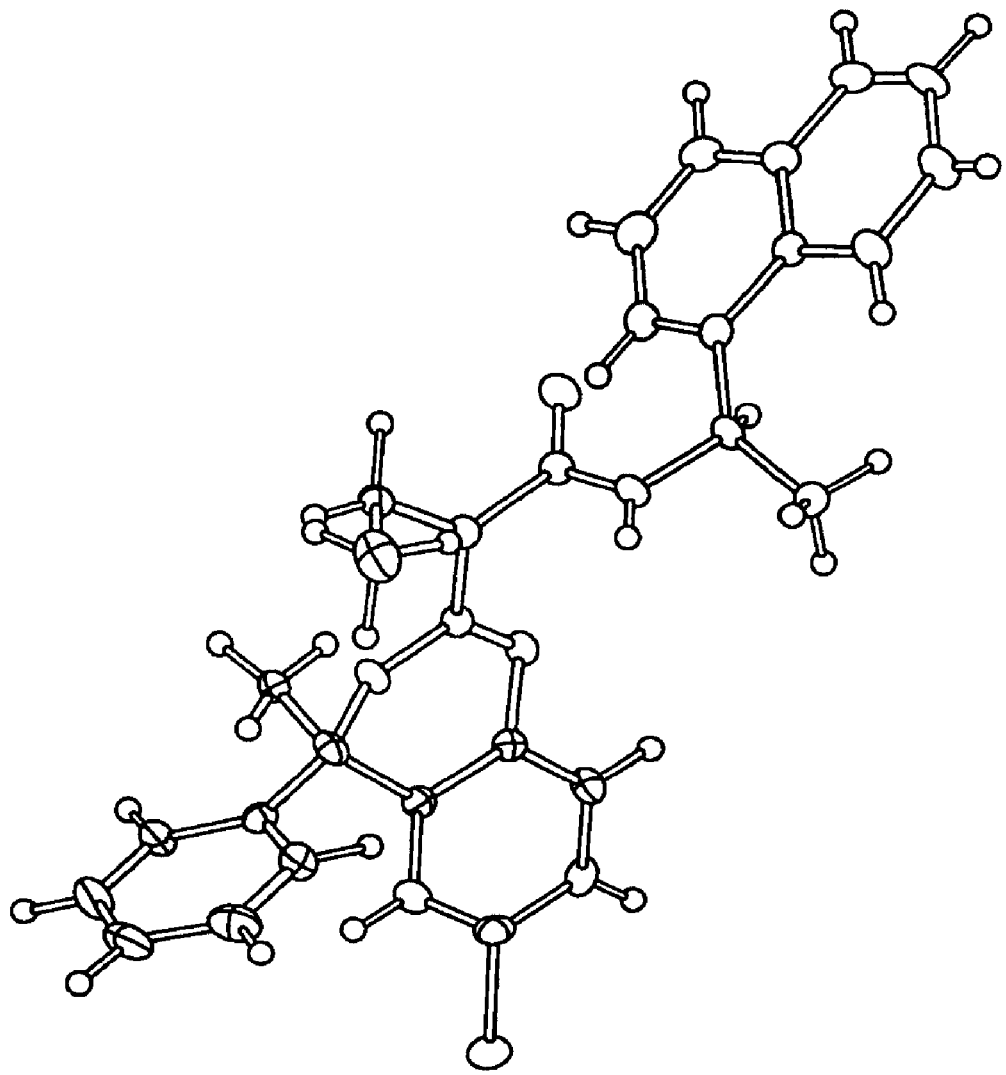
FIG. 8 provides X-crystal structure of the adduct of R-etifoxine obtained in Example 4.

X-ray analysis was performed (see FIG. 8) on the adduct and the absolute configuration of enantiomerically pure etifoxine peak 1 was determined to be (R). Peak 2 was assigned to be the corresponding S-etifoxine.

Example 5

Optical Rotation of Pure Enantiomers of Etifoxine

Figure 3A:
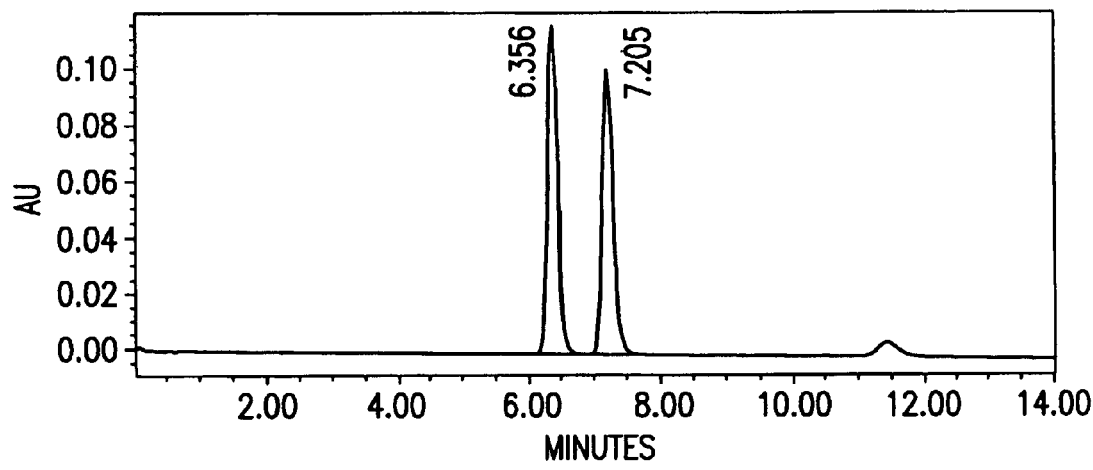
FIG. 3A provides an HPLC trace of etifoxine enantiomers.
Figure 3B:
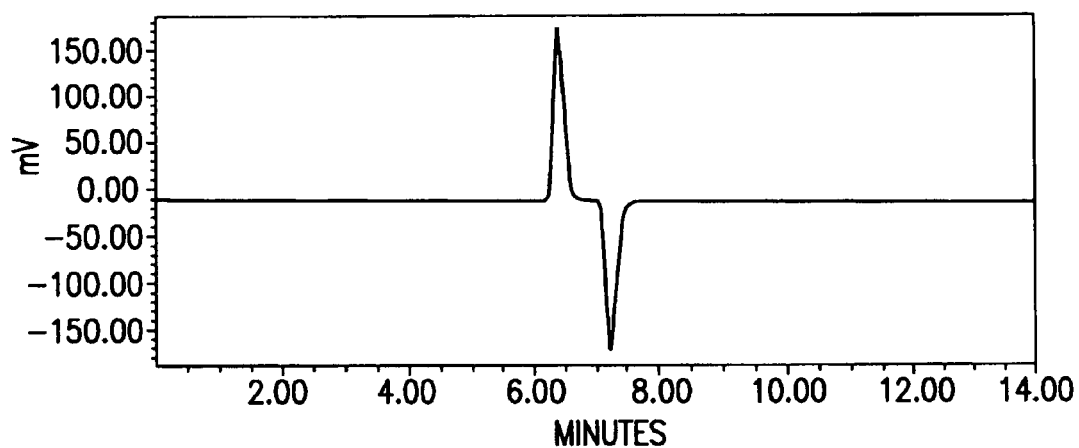
FIG. 3B provides an optical rotation trace of R-etifoxine and S-etifoxine.

Racemic etifoxine was separated by chiral HPLC using a CHIRALCEL® ODH 4.6 mm×250 mm column. The separation was carried out with hexane/ethanol (95:5 by volume) as an eluent. The flow rate was set at 1 ml/min at 25° C. The compounds were detected by UV absorbance. Baseline separation was achieved as shown in FIG. 3A. Polarimetry detection at 230 nm (FIG. 3B) indicates that peak 1 is R-etifoxine and that peak 2 is S-etifoxine. As shown in FIG. 3B, R-etifoxine has an optical rotation of about 170° and S-etifoxine has an optical rotation of about −165°.

Example 6

Measurement of GABA Subunit Selectivity Based on Modulation of the GABA-Evoked Currents in *Xenopus* Oocytes GABA subunit selectivity of etifoxine enantiomers was measured based on their ability to modulate the GABA-evoked currents in *Xenopus* oocytes.

Receptor mRNA preparation: cDNA clones encoding human $GABA_A$ receptor subunits were obtained from commercial sources. mRNA was prepared using conventional techniques with commercially-available "mMessage machine" kits (Ambion). Individual mRNAs (~1 μg/μL) were stored in aliquots at −80° C.

mRNA injections into *Xenopus* oocytes: Preparation and micro-injection of oocytes were performed as reported in detail previously (see, Whittemore et al., 1996, *Mol Pharmacol* 50: 1364-1375). Individual oocytes were injected with 5-50 ng of mRNA at 5:1:1 (GABA). For example, individual oocytes were injected with a 5:1:1 mixture of α1, β1-3, and γ2L (~5-50 ng of each subunit per cell) to produce expression of α1β1-3γ2L $GABA_A$ receptors. Following injections, oocytes were maintained at 16-17° C. in Barth's medium containing (in mM): NaCl, 88; KCl, 1; $CaCl_2$, 0.41; $Ca(NO_3)_2$, 0.33; $MgSO_4$, 0.82; $NaHCO_3$, 2.4; HEPES 5; pH=7.4, with 0.1 mg/ml gentamycin sulfate.

Oocyte Electrophysiological recordings: Individual oocytes were placed on a nylon mesh in a 35 mm dish, perfused with frog Ringer (see, Whittemore et al., supra), and voltage clamped at a holding potential of −70 mV. In some cases, simple voltage steps were made to test voltage-dependence. Oocytes were perfused with fresh Ringer or exposed to GABA ±modulators using a custom-made gravity-driven perfusion system consisting of a linear array of 3 capillary tubes. The concentration of GABA used to evoke control currents was adjusted for each individual oocyte to be ~10% of the maximal current ($EC_{10}$) measured in that cell. The concentration of GABA required to evoke $EC_{10}$ 'control' currents varied between ~2 and 12 μM. Once stable GABA $EC_{10}$ control responses were obtained, oocytes were exposed to modulator compounds (e.g., etifoxine enantiomers) for 20-40 seconds before a co-application with the control GABA solution. Data are expressed as % of control currents (% modulation=100*[(modulated current/GABA control current)−1].

Figure 4A:
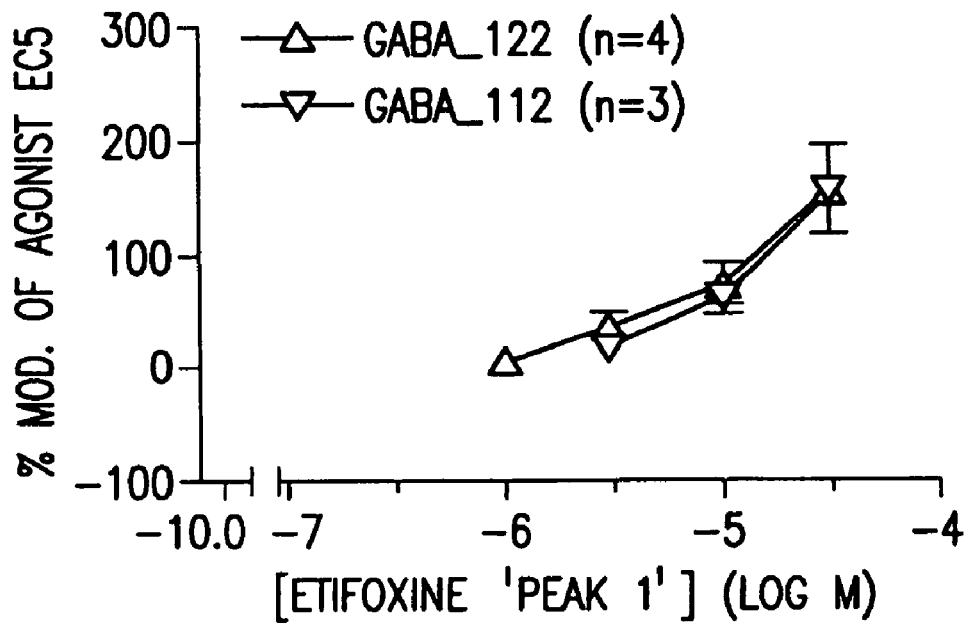
FIG. 4A provides GABA subunit selectivity of R-etifoxine using a 2-electrode clamp technique.
Figure 4B:
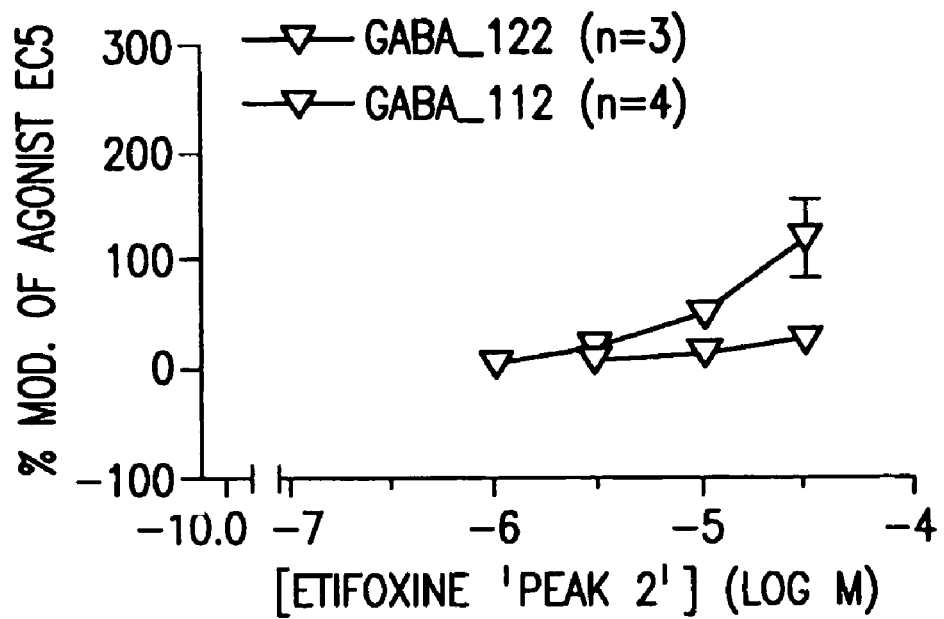
FIG. 4B provides GABA subunit selectivity of S-etifoxine using a 2-electrode clamp technique.

As seen in FIGS. 4A and 4B, S-etifoxine shows selectivity for GABA receptor comprising β subunit while R-etifoxine shows little or no GABA subunit selectivity in this assay. The S enantiomer is more selective for β2 subunit than β1 subunit.

Example 7

In Vivo Analgesic Effect of Etifoxine Enantiomers in Formalin Test

The analgesic effect of test compounds was assessed in a mouse formalin pain model (Hole et al., 1993, *Pain* 53:247-254). Male NSA mice weighing between 27 and 30 g were housed with access to food and water ad libitum until the test date. On the day of testing, they were given a period of 1 h to adjust to the test chamber. Test compounds or vehicle control (75% polyethylene glycol in 5% dextrose+water) were administered i.p. at 30 minutes prior to the administration of formalin. A solution of 20 μl of 2.5% formalin was then injected subcutaneously into the dorsal side of the hind paw of the test mouse. Immediately following formalin injection, the mice were observed over the next 50 min and the time spent licking the injected hind paw was recorded. The observation time was broken down into 5 minute "bins", with 10 bins in total. The first 5-min bin is the early phase, considered to be reflective of acute pain. Bins three to ten make up the late phase, considered a measure of chronic inflammatory pain. The results for the late phase are expressed as the averaged mean time (in seconds) that mice spent licking in a 5-min period.

Dose-response relationship was conducted in the range of 3 to 60 mg/kg. Statistical differences in response were determined by one-way analysis of variance with the Dunnett's post-hoc test by using the Prism3 statistical software (Graph-Pad, Inc., San Diego, Calif.).

Figure 5:
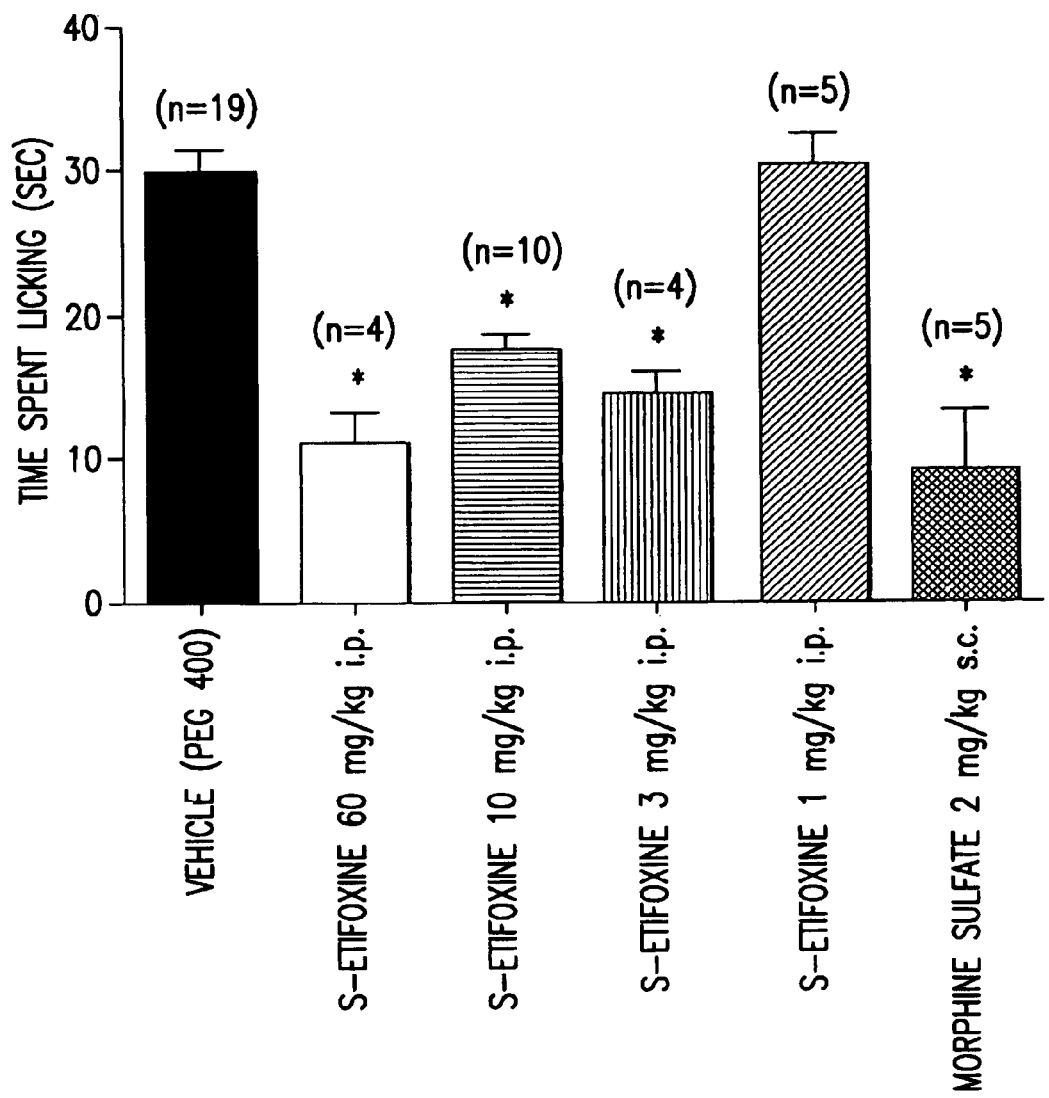
FIG. 5 illustrates the effect of S-etifoxine on late phase licking in the mouse formalin test.

As seen in FIG. 5, S-etifoxine is active in the formalin test at 3 mg/kg.

Example 8

In Vivo Racemization Study

Pure S-etifoxine was administered at 30 mg/kg, perorally, to NSA mice. The desired enantiomer was dissolved in PEG at a concentration of 15 mg/mL and a dose of 2 mL/kg was administered perorally to overnight fasted mice. Plasma concentration of etifoxine enantiomers was determined by LC-MS/MS analysis.

A mixture of 100 μL plasma and 200 μL water in a 6-mL plastic culture tube was vortexed briefly, for about 10 seconds. To this was added 1.5 mL methyl tert-butyl ether and 1.5 mL hexane and vortexed briefly for about 10 seconds. The mixture was centrifuged for about 10 minutes and frozen at −80° C. for 10 minutes. The organic layer was collected and dried under nitrogen at 37° C. The solid was resuspended in 250 μL methanol, vortexed and transferred to 96-well plate.

Figure 6A:
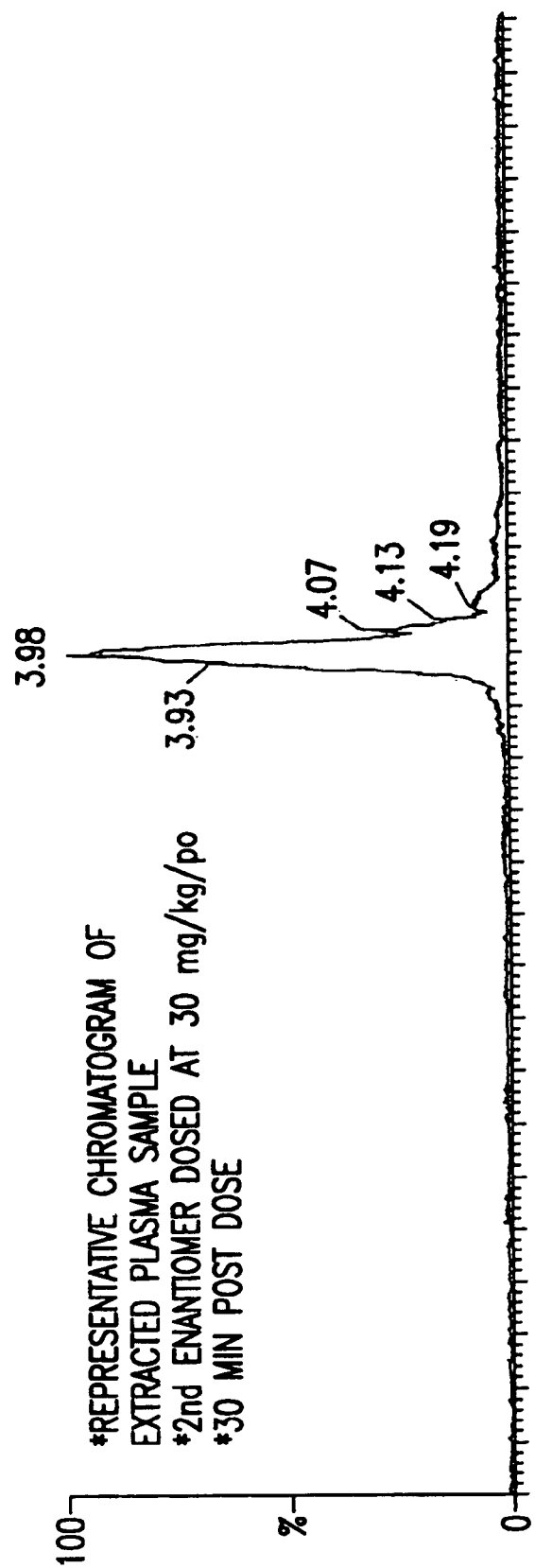
FIG. 6A provides representative chromatogram of a plasma sample extracted 30 minutes following a 30 mg/kg/po dose of S-etifoxine.
Figure 6B:
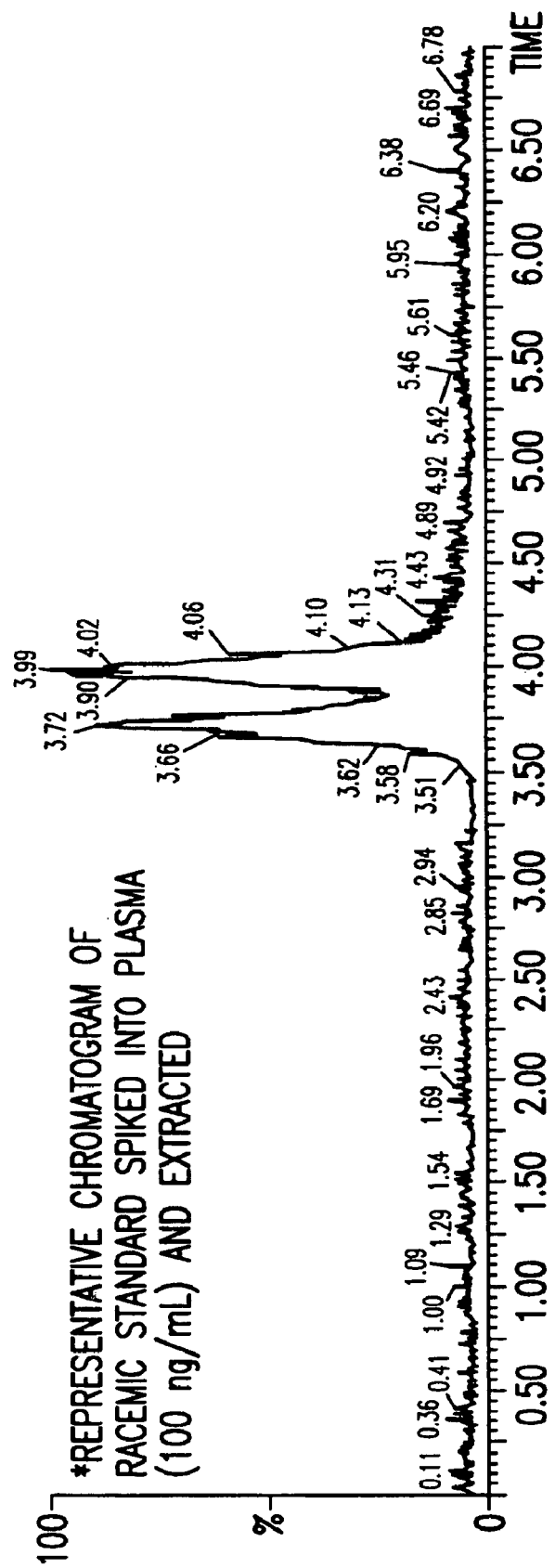
FIG. 6B provides representative chromatogram of racemic etifoxine spiked into plasma at 100 ng/mL.
Figure 7A:
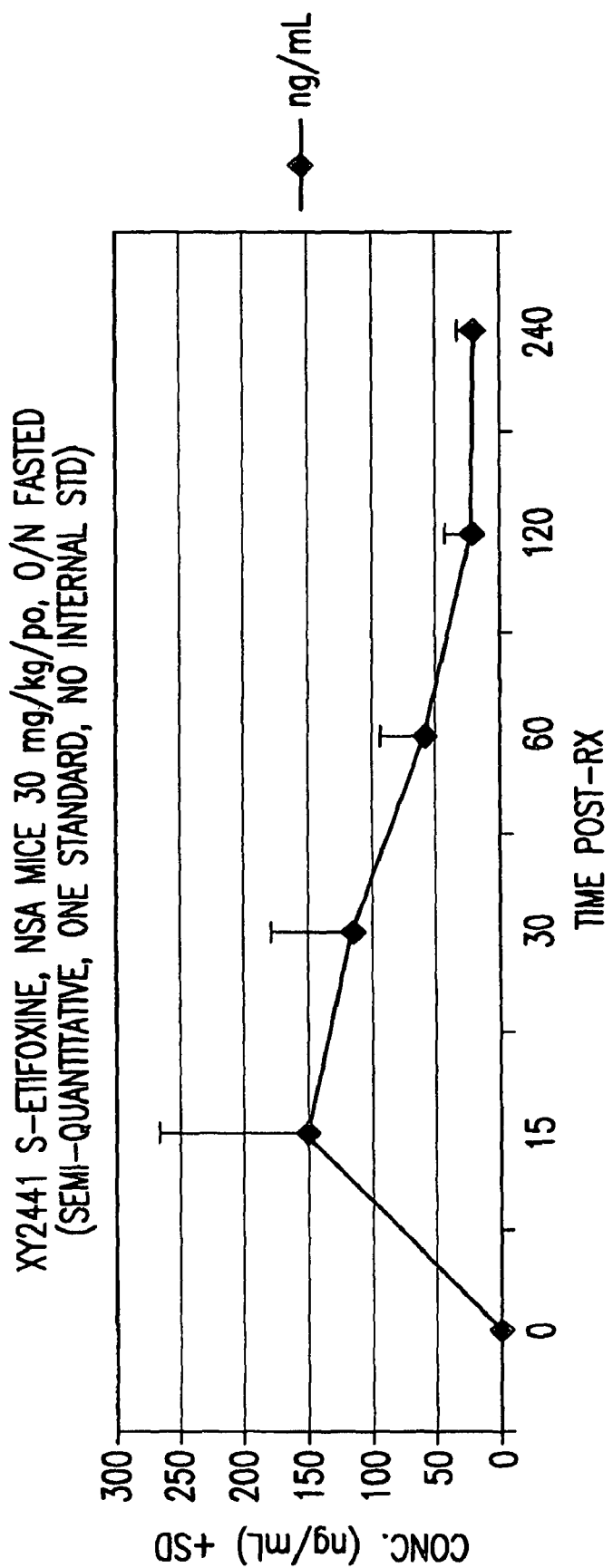
FIGS. 7A and 7B provide plots of plasma concentration of S-etifoxine over time.
Figure 7B:
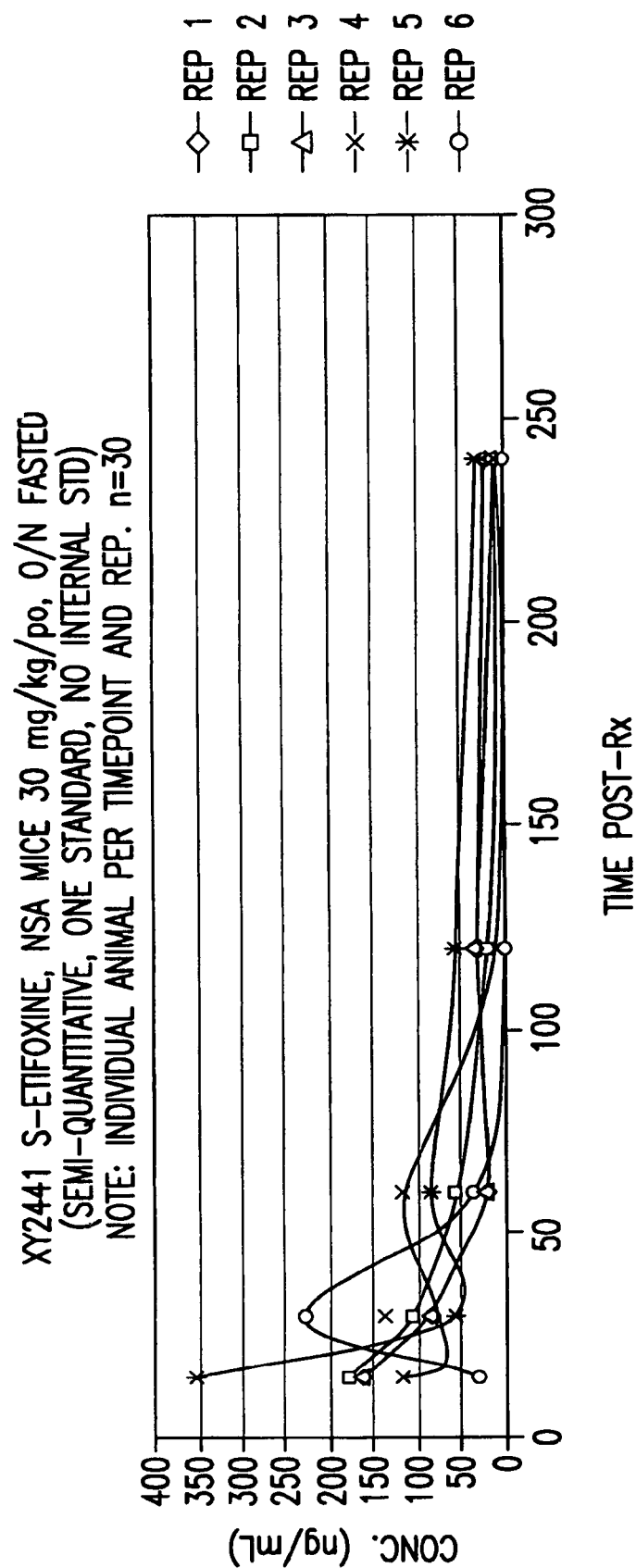

The samples were analyzed by LC-MS/MS on a 460 mm×250 mm CHIRALCEL® OD (lot #OD00CE-FJ033) column at room temperature. A mixture of 75% hexane, 25% isopropyl alcohol and 0.05% diethylaniline was used as an isocratic mobile phase. The flow rate was set at 1 mL/min at room temperature. Racemic etifoxine spiked into plasma was used as a reference standard. FIGS. 6A and 6B provide representative chromatograms of extracted plasma sample (pure S-etifoxine, dosed at 30 mg/kg/po at 30 minutes post dose) and racemic standard spiked into plasma (100 ng/mL), respectively. As seen in FIG. 6A, the extracted plasma spiked with pure S-etifoxine shows predominantly pure S-etifoxine and no detectable R-etifoxine, indicating little or no racemization in vivo. For comparison, FIG. 6B provides a chromatogram of extracted plasma spiked with racemic etifoxine. FIGS. 7A and 7B provide plots of plasma concentration of S-etifoxine enantiomer with time.

Example 9

Tablets

Tablets, each containing 50 milligrams of S-etifoxine, can be prepared in the following manner:

| Composition (for 1000 tablets) | |
|---|---|
| S-etifoxine | 50.00 grams |
| Mannitol | 150.33 grams |
| Lactose | 100.00 grams |
| Talc | 10.40 grams |
| Glycine | 8.3 grams |
| Stearic acid | 6.6 grams |
| Saccharin | 1.0 grams |
| 5% Gelatin solution q.s. | |

The solid ingredients are each forced through a 0.25 mm mesh sieve. The mannitol and the lactose are mixed, granulated with the addition of gelatin solution, forced through a 2 mm mesh sieve, dried at 50° C. and forced through a 1.7 mm mesh sieve. The S-etifoxine, glycine and saccharin are carefully mixed, the granulated mannitol and lactose, stearic acid and talc added and the whole mixed thoroughly. The mass is compressed to form tablets of approximately 5 mm diameter which are concave on both sides and have a breaking groove on the one side.

Example 10

Tablets

Tablets, each containing 100 milligrams of S-etifoxine, can be prepared in the following manner: composition (for 1000 tablets)

| Composition (for 1000 tablets) | |
|---|---|
| S-etifoxine | 100.00 grams |
| Lactose | 3285.0 grams |
| Corn starch | 170.5 grams |
| Polyethylene glycol 6000 | 50.0 grams |
| Talc | 250.0 grams |
| Magnesium stearate | 40.0 grams |
| Demineralized water q.s. | |

The solid ingredients are first forced through a 0.6 mm mesh sieve. Then the S-etifoxine, lactose, talc, magnesium stearate and half of the starch are intimately mixed. The other half of the starch is suspended in 650 milliliters of water and this suspension is added to a boiling solution of the polyethylene glycol in 2600 milliliters of water. The resulting paste is added to the pulverulent substances, and the whole is mixed and granulated, if necessary with the addition of water. The granulate is dried overnight at 35° C., forced through a sieve of 1.2 mm mesh and compressed to form tablets of approximately 5 mm diameter which are concave on both sides and have a breaking notch on the upper side.

Example 11

Gelatin Dry-Filled Capsules

Gelatin dry-filled capsules, each containing 100 milligrams of S-etifoxine, can be prepared in the following manner:

| Composition (for 1000 capsules) | |
|---|---|
| S-etifoxine | 100.0 grams |
| Microcrystalline cellulose | 120.0 grams |
| Sodium lauryl sulfate | 8.0 grams |
| Magnesium stearate | 2.0 grams |

The sodium lauryl sulfate is sieved into the S-etifoxine through a 0.2 mm mesh sieve and the two components intimately mixed for 10 minutes. The micro-crystalline cellulose is then added through a 0.9 mm mesh sieve and the whole again intimately mixed for 10 minutes. Finally, the magnesium stearate is added through a 0.8 mm mesh sieve and, after mixing for a further 3 minutes, the mixture is introduced in portions of 28 milligrams each into gelatin dry-fill capsules.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. Enantiomerically pure S-etifoxine, or a pharmaceutically acceptable salt thereof, wherein the enantiomerically pure S-etifoxine is at least 80% by weight S-etifoxine and at most 20% by weight R-etifoxine based on total weight of etifoxine.

2. The compound of claim 1, wherein the compound is a salt.

3. The compound of claim 2, wherein the salt is a hydrochloride salt.

4. A pharmaceutical composition comprising the compound claim 1, or a pharmaceutically acceptable salt thereof, and a pharmaceutical carrier, excipient or diluent.

5. The pharmaceutical composition of claim 4 that is formulated for oral administration.

6. The pharmaceutical composition of claim 5 that is formulated as an oral capsule or a tablet.

7. The pharmaceutical composition of claim 4 that is formulated for topical administration.

8. The pharmaceutical composition of claim 7 that is formulated as a gel.

9. A pharmaceutical unit dosage comprising the pharmaceutical composition of claim 5.

10. A method for modulating activity of $GABA_A$ receptor comprising contacting the receptor with an effective amount of the compound of claim 1, or a pharmaceutically acceptable salt thereof.

11. The method of claim 10 wherein $GABA_A$ receptor comprising subunit $\beta 2$ is selectively modulated relative to $GABA_A$ receptor comprising subunit $\beta 1$.

12. A method of treating, ameliorating or managing symptoms associated with a disease comprising administering to a subject in need thereof an effective amount of a compound of claim 1, or a pharmaceutically acceptable salt thereof, wherein the subject has a disease selected from anxiety, multiple sclerosis, muscle relaxation in spinal spasticity, cerebral palsy, trigeminal neuralgia, pain and drug withdrawal symptoms.

13. A method of treating, ameliorating or managing a gut motility disorder comprising administering to a subject having gut motility disorder an effective amount of a compound of claim 1, or a pharmaceutically acceptable salt thereof.

14. A method of treating, ameliorating or managing anxiety comprising administering to a subject in need thereof an effective amount of a compound of claim 1, or a pharmaceutically acceptable salt thereof.

15. The method of claim 10, wherein the compound is administered as an oral or topical formulation.

16. The method of claim 15, wherein the oral formulation is a capsule.

17. The method of claim 15, wherein the topical formulation is a gel.

18. The method of claim 12, wherein the amount of the compound administered is about 1 mg up to about 2000 mg/day.

19. The method of claim 12, wherein the amount of the compound administered is about 10 mg up to about 1000 mg/day.

20. The method of claim 12, wherein the amount of the compound administered is about 13 mg up to about 800 mg/day.

21. The method of claim 12, wherein the amount of the compound administered is about 15 mg up to about 300 mg/day.

22. The method of claim 12, wherein the amount of the compound administered is about 25 mg up to about 200 mg/day.

23. The method of claim 12, wherein the amount of the compound administered is about 50 mg up to about 150 mg/day.

24. The method of claim 12, wherein the amount of the compound administered is about 50 mg/day.

25. The method of claim 12, wherein the amount of the compound administered is about 100 mg/day.

26. The method of claim 12, wherein the amount of the compound administered is about 150 mg/day.

27. The method of claim 12 further comprising administering an additional anxiolytic drug to the patient.

28. The method of claim 27, wherein the additional anxiolytic drug is selected from Buspirone, Gepirone, Ipsapirone, Tondospirone, Alprazolam, Bromazepam, Camazepam, Chlordiazepoxide, Clobazam, Clorazepate, Chotiazepam, Cloxazolam, Diazepam, Ethyl Loflazepate, Etizolam, Fluidazepam, Flutazolam, Flutoprazepam, Halazepam, Ketazolam, Lorazepam, Loxapine, Medazepam, Metaclazepam, Mexazolam, Nordazepam, Oxazepam, Oxazolam, Pinazepam, Prazepam, Tofisopam, Cyclarbamate, Emylcamate, Hydroxyphenamate, Meprobamate, Phenprobamate, Tybamate, Alpidem, Benzoctamine, Captodiamine, Chlormezanone, Flesinoxan, Fluoresone, Glutamic Acid, Hydroxyzine, Lesopitron, Mecloralurea, Mephenoxalone, Mirtazepine, Oxanamide, Phenaglycodol, Suriclone and Zatosetron.

29. The method of claim 12 wherein said administration causes reduced sedation in the subject compared to a comparable dose of racemic etifoxine.

30. The method of claim 14, wherein the amount of the compound administered is about 1 mg up to about 2000 mg/day.

31. The method of claim 14, wherein the amount of the compound administered is about 10 mg up to about 1000 mg/day.

32. The method of claim 14, wherein the amount of the compound administered is about 13 mg up to about 800 mg/day.

33. The method of claim 14, wherein the amount of the compound administered is about 15 mg up to about 300 mg/day.

34. The method of claim 14, wherein the amount of the compound administered is about 25 mg up to about 200 mg/day.

35. The method of claim 14, wherein the amount of the compound administered is about 50 mg up to about 150 mg/day.

36. The method of claim 14, wherein the amount of the compound administered is about 50 mg/day.

37. The method of claim 14, wherein the amount of the compound administered is about 100 mg/day.

38. The method of claim 14, wherein the amount of the compound administered is about 150 mg/day.

39. The method of claim 14 further comprising administering an additional anxiolytic drug to the patient.

40. The method of claim 39, wherein the additional anxiolytic drug is selected from Buspirone, Gepirone, Ipsapirone, Tondospirone, Alprazolam, Bromazepam, Camazepam, Chlordiazepoxide, Clobazam, Clorazepate, Chotiazepam, Cloxazolam, Diazepam, Ethyl Loflazepate, Etizolam, Fluidazepam, Flutazolam, Flutoprazepam, Halazepam, Ketazolam, Lorazepam, Loxapine, Medazepam, Metaclazepam, Mexazolam, Nordazepam, Oxazepam, Oxazolam, Pinazepam, Prazepam, Tofisopam, Cyclarbamate, Emylcamate, Hydroxyphenamate, Meprobamate, Phenprobamate, Tybamate, Alpidem, Benzoctamine, Captodiamine, Chlormezanone, Flesinoxan, fluoresone, Glutamic Acid, Hydroxyzine, Lesopitron, Mecloralurea, Mephenoxalone, Mirtazepine, Oxanamide, Phenaglycodol, Suriclone and Zatosetron.

41. The method of claim 14, wherein said administration causes reduced sedation in the subject compared to a comparable dose of racemic etifoxine.

42. The method of claim 14, wherein said administration causes reduced sedation in the subject compared to a comparable dose of racemic etifoxine.

43. The compound of claim 1, wherein the enantiomerically pure S-etifoxine is at least 90% by weight S-etifoxine and at most 10% by weight R-etifoxine based on total weight of etifoxine.

44. The compound of claim 1, wherein the enantiomerically pure S-etifoxine is at least 97% by weight S-etifoxine and at most 3% by weight R-etifoxine based on total weight of etifoxine.

45. The method of claim 12, wherein the treatment is for anxiety and wherein the enantiomerically pure S-etifoxine is at least 97% by weight S-etifoxine and at most 3% by weight R-etifoxine based on total weight of etifoxine.

46. The method of claim 12, wherein the treatment is for pain and wherein the enantiomerically pure S-etifoxine is at least 97% by weight S-etifoxine and at most 3% by weight R-etifoxine based on total weight of etifoxine.

47. The compound of claim 1, wherein the pharmaceutically acceptable salt is selected from the group consisting of hydrochloric, hydrobromic, hydroiodic, nitric, sulfuric, and phosphoric.

* * * * *